United States Patent [19]

Hayakawa et al.

[11] Patent Number: 5,248,655
[45] Date of Patent: Sep. 28, 1993

[54] 1,2,4-TRIAZOLE-3-YL-ALKANE- OR CYCLOALKANE-PHOSPHONIC ACIDS AS ACTIVE SUBSTANCES IN WEED KILLERS

[75] Inventors: Kenji Hayakawa, Takarazuka; Ichiro Mori, Ashiya; Genji Iwasaki, Takarazuka; Shin-Ichiro Matsunaga, Amagasaki, all of Japan

[73] Assignee: Japat Ltd., Basle, Switzerland

[21] Appl. No.: 925,755

[22] Filed: Aug. 7, 1992

[30] Foreign Application Priority Data

Aug. 9, 1991 [GB] United Kingdom ............... 9117314
Apr. 14, 1992 [GB] United Kingdom ............... 9208253

[51] Int. Cl.⁵ .................... A01N 57/24; C07F 9/6518
[52] U.S. Cl. .................... 504/197; 548/119; 546/22
[58] Field of Search ............. 548/119; 546/22; 71/92; 504/197

[56] References Cited

FOREIGN PATENT DOCUMENTS 065216 11/1982 European Pat. Off.
0078613 5/1983 European Pat. Off.
2114133 8/1983 United Kingdom.
2158071 11/1985 United Kingdom.

OTHER PUBLICATIONS

Pudovik et al., Chem. Abstr., vol. 52, p. 3713 (1958).
Polya, Comprehensive Heterocyclic Chemistry 1984, vol. 5, pp. 733-790.
Morita et al., Bull. Chem. Soc. Japan, vol. 51(7) 2169-2170 (1978).
Katritzky et al., Tetrahedron, vol. 46, No. 2, pp. 641-648 (1990).
Tenlade et al., Synthesis, 1987, pp. 1037-1039.
Satchell et al., Chem. Soc. Rev. 4, 231-250 (1975).
Sonntag. Chem. Rev. 1953, 52 pp. 237-416.
Anderson et al., J. Heterocyclic Chem. 23, 1257-1262 (1986).
Hammerschmidt et al., Liebigs Ann. Chem. 1979, 492-502.
Öhler et al., Monatsheft für Chemie, 116, 77-86 (1985).
Harvey, Tetrahedron, 1966, vol. 22, pp. 2561-2573.
Hoffmann, Synthesis, 1988, pp. 62-64.

*Primary Examiner*—Patricia L. Morris
*Attorney, Agent, or Firm*—Wenderoth, Lind & Ponack

[57] ABSTRACT

A triazole of the formula I

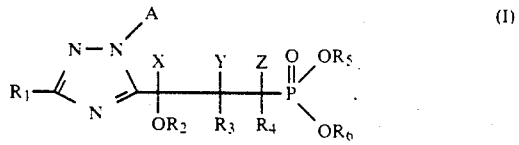

in which the meanings of the radicals are described in claim 1, have a herbicidal and plant-growth regulating action. They are suitable as active substances in weed killers and in compositions for positively influencing the growth of crop plants.

20 Claims, No Drawings

1,2,4-TRIAZOLE-3-YL-ALKANE- OR CYCLOALKANE-PHOSPHONIC ACIDS AS ACTIVE SUBSTANCES IN WEED KILLERS

The present invention relates to novel triazoles which have a herbicidal action and are plant-growth-regulating, to processes for their preparation, to compositions containing them as active substances, and to their use for controlling weeds, especially selectively in crops, or for regulating and inhibiting plant growth.

Triazole compounds which have a herbicidal action are generally known. For example, European Patent Application No. 0 078 613 describes herbicidally active triazole compounds.

It has been found that compounds of the formula (I) have a herbicidal and plant-growth-regulating action. They are therefore suitable as active substances in weed killers and in compositions for positively influencing the growth of crop plants.

The triazoles according to the invention are those of the formula I

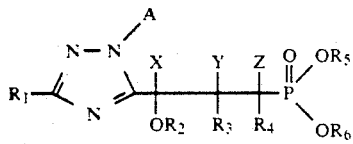

in which

A is hydrogen, $C_1$-$C_4$-alkyl, $C_1$-$C_4$-alkenyl, triphenylmethyl, benzyl, a group

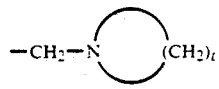

or $C_1$-$C_4$-alkyl substituted by hydroxy or $C_1$-$C_4$-alkoxy;
t is 4 or 5;
$R_1$ is hydrogen, fluorine or $C_1$-$C_4$-alkyl;
$R_2$ is hydrogen, a group

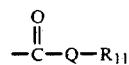

or a group

$R_3$ is hydrogen or $C_1$-$C_4$-alkyl;
$R_4$ is hydrogen or $C_1$-$C_4$-alkyl, or $R_3$ and $R_4$ together represent a chemical bond;
$R_5$ is hydrogen, $C_1$-$C_4$-alkyl, benzyl or an alkali metal, alkaline earth metal, ammonium, organic ammonium, trialkylsulphonium, trialkylsulfoxonium, phosphonium or amidinium cation;
$R_6$ is hydrogen, $C_1$-$C_4$-alkyl, benzyl or an alkali metal, alkaline earth metal, ammonium, organic ammonium, trialkylsulphonium, trialkylsulfoxonium, phosphonium or amidinium cation;
X is hydrogen, $C_1$-$C_4$-alkyl, $C_3$-$C_6$-cycloalkyl, $C_1$-$C_4$-haloalkyl, $C_1$-$C_4$-alkyl substituted by hydroxy or $C_1$-$C_4$-alkyl substituted by $-OR_{14}$;
Y is hydrogen or $C_1$-$C_4$-alkyl or together with X a $-CH_2-(CH_2)_p-CH_2-$ group or together with Z a $C_1$-$C_4$-alkylene bridge which is substituted by $R_7$ and $R_8$;
Z is hydrogen or $C_1$-$C_4$-alkyl or together with X a $C_2$-$C_4$-alkylene bridge which is substituted by $R_7$ and $R_8$;
Q is oxygen, sulfur or $NR_{10}$;
$R_7$ is hydrogen, $C_1$-$C_4$-alkoxy or $C_1$-$C_4$-alkyl;
$R_8$ is hydrogen, $C_1$-$C_4$-alkoxy or $C_1$-$C_4$-alkyl;
$R_9$ is $C_1$-$C_6$-alkyl, $C_2$-$C_6$-alkenyl; $C_2$-$C_6$-alkynyl; or $C_1$-$C_6$-alkyl, $C_2$-$C_6$-alkenyl, $C_2$-$C_6$-alkynyl substituted by halogen or $C_1$-$C_4$-alkoxy; or phenyl, benzyl; or phenyl, benzyl substituted by $C_1$-$C_4$-alkyl, halogen, $C_1$-$C_4$-haloalkyl, $C_1$-$C_4$-alkoxy, cyano, nitro, $C_1$-$C_4$-alkoxycarbonyl or $S(O)_m$-$C_1$-$C_4$-alkyl; or is $C_1$-$C_6$-alkoxyalkyl, $C_1$-$C_6$-alkylcarbonyloxyalkyl, $C_1$-$C_6$-alkoxycarbonylalkyl or $C_3$-$C_6$-cycloalkyl;
$R_{10}$ is hydrogen, $C_1$-$C_6$-alkyl, $C_1$-$C_6$-alkoxy, $C_2$-$C_6$-alkenyl, $C_3$-$C_6$-alkynyl; or $C_1$-$C_6$-alkyl, $C_2$-$C_6$-alkenyl, $C_3$-$C_6$-alkynyl substituted by halogen or $C_1$-$C_4$-alkoxy;
$R_{11}$ is $C_1$-$C_6$-alkyl, $C_3$-$C_6$-alkenyl, $C_3$-$C_6$-alkynyl; or $C_1$-$C_6$-alkyl, $C_3$-$C_6$-alkenyl, $C_3$-$C_6$-alkynyl substituted by halogen or $C_1$-$C_4$-alkoxy; or phenyl, benzyl; or phenyl, benzyl substituted by $C_1$-$C_4$-alkyl, halogen, halomethyl, $C_1$-$C_4$-alkoxy, cyano, nitro, $C_1$-$C_4$-alkoxycarbonyl or $S(O)_n$-$C_1$-$C_4$-alkyl;
$R_{14}$ is hydrogen, a group

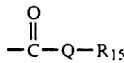

or a group

$R_{15}$ is $C_1$-$C_6$-alkyl, $C_3$-$C_6$-alkenyl, $C_3$-$C_6$-alkynyl; or $C_1$-$C_6$-alkyl, $C_3$-$C_6$-alkenyl, $C_3$-$C_6$-alkynyl substituted by halogen or $C_1$-$C_4$-alkoxy; or phenyl, benzyl; or phenyl, benzyl substituted by $C_1$-$C_4$-alkyl, halogen, halomethyl, $C_1$-$C_4$-alkoxy, cyano, nitro, $C_1$-$C_4$-alkoxycarbonyl or $S(O)_n$-$C_1$-$C_4$-alkyl;
$R_{16}$ is $C_1$-$C_6$-alkyl, $C_2$-$C_6$-alkenyl, $C_2$-$C_6$-alkynyl; or $C_1$-$C_6$-alkyl, $C_2$-$C_6$-alkenyl, $C_2$-$C_6$-alkynyl substituted by halogen or $C_1$-$C_4$-alkoxy; or phenyl, benzyl; or phenyl, benzyl substituted by $C_1$-$C_4$-alkyl, halogen, $C_1$-$C_4$-haloalkyl, $C_1$-$C_4$-alkoxy, cyano, nitro, $C_1$-$C_4$-alkoxycarbonyl or $S(O)_m$-$C_1$-$C_4$alkyl; or is $C_1$-$C_6$-alkoxyalkyl, $C_1$-$C_6$-alkylcarbonyloxyalkyl, $C_1$-$C_6$-alkoxycarbonylalkyl or $C_3$-$C_6$-cycloalkyl;
m is 0, 1 or 2;
n is 0, 1 or 2;
p is 1 or 2;
with the proviso that $R_1$, $R_2$, $R_3$, $R_4$, X, Y and Z are not simultaneously hydrogen; and if $R_1$, $R_3$, $R_4$, X, Y and Z are simultaneously hydrogen, $R_9$ is not methyl.

In the above definitions, halogen is to be understood as being fluorine, chlorine, bromine and iodine, preferably fluorine, chlorine and bromine.

Alkyl is, for example, methyl, ethyl, isopropyl, n-propyl, n-butyl, isobutyl, sec-butyl, tert-butyl and the various isomeric pentyl or hexyl radicals.

Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl.

Alkoxy is, for example, methoxy, ethoxy, propoxy, isopropoxy, n-butoxy, isobutoxy, sec-butoxy and tert-butoxy; preferably methoxy.

Alkenyl is to be understood as being straight-chain or branched alkenyl, for example vinyl, allyl, methallyl, 1-methylvinyl, but-2-en-1-yl, 3-pentenyl, 2-hexenyl or 3-heptenyl. Alkenyl radicals having a chain length of 2 or 3 carbon atoms are preferred.

The alkynyl radicals occurring in the definitions of the substituents may be straight-chained or branched, for example ethynyl, propargyl, 3-butynyl, 1-methylpropargyl, 2-pentynyl or 2-hexynyl. Ethynyl and propargyl are preferred.

Alkoxycarbonyl is, for example: methoxycarbonyl, ethoxycarbonyl, n-propoxycarbonyl, isopropoxycarbonyl and n-butoxycarbonyl, preferably methoxycarbonyl and ethoxycarbonyl.

If the compounds of the formula I contain an asymmetric carbon atom, this results in the fact that the compounds can occur in optically isomeric forms. If there is an aliphatic C=C double bond, geometric isomerism can also occur. The formula I therefore also embraces all stereoisomers which are possible and which are in the form of enantiomers, diastereomers or their mixtures.

For compounds of the formula I, which are cyclic phosphonates, stereoisomers of the following formulae are obtained:

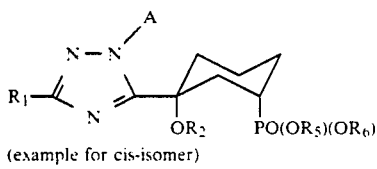
(example for cis-isomer)

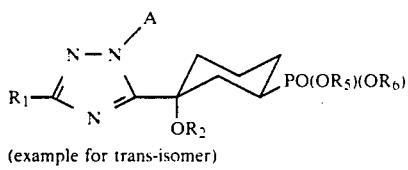
(example for trans-isomer)

The configuration of the above mentioned examples of stereoisomers of compounds of the formula I is defined according to the position of the $OR_2$ group and $PO(OR_5)(OR_6)$ group.

This invention includes all of the tautomeric isomers represented by the following formula of resonance structure:

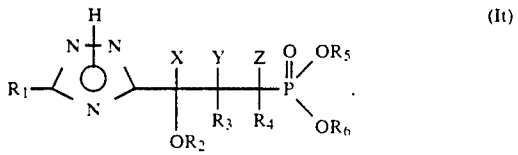
(It)

The term organic ammonium cation is intended to include ammonium cations prepared from low molecular weight amines, that is to say those having a molecular weight below about 300. Examples of such amines include alkylamines, alkenylamines, and alkanolamines containing not more than two amino groups, such as methylamine, ethylamine, n-propylamine, iso-propylamine, the four isomeric butylamines, n-amylamine, iso-amylamine, hexylamine, heptylamine, octylamine, nonylamine, decylamine, pentadecylamine, hexadecylamine, heptadecylamine, octadecylamine, methylethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylendiamine, diethanolamine, tri-iso-propylamine, tri-n-butylamine, tri-iso-butylamine, tri-sec.-butylamine, tri-n-amylamine, trimethylamine, triethylamine, tripropylamine; heterocyclic amines as, for example, pyridine, chinoline, iso-chinoline, morpholine, piperidine, pyrrolidine, indoline, chinuclidine and azepine; primary arylamines as, for example, aniline, methoxyaniline, ethoxyaniline, o,m,p-toluidine, phenylendiamine, benzidine, naphthylamine and o,m,p-chloroaniline; in particular ethyl-, propyl-, diethyloder triethylamine, preferably iso-propylamine and diethanolamine.

Tetra-substituted ammonium cations are also included, for example tetramethylammonium, tetrabutylammonium, benzyltrimethylammonium, benzyltriethylammonium, tetra-ethylammonium and trimethylethylammonium cations.

Trialkylsulfonium cations include those, for example, in which each of the three alkyl groups, which are not necessary all the same, may contain from 1 to 6 carbon atoms. Trialkylsulfoxonium cations likewise include those in which each of the three alkyl groups, which may be the same or different, may contain from 1 to 6 carbon atoms.

Phosphonium cations include, for example, cations in which the phosphorus atom bears four substituents, each of which may be an alkyl group of one to ten carbon atoms or a phenyl group, for example, the tetramethylphosphonium, tetrabutylphosphonium, and tetraphenylphosphonium cations.

Amidinium cations include, for example, straight chain amidinium cations of formula $R_{14}-C(NH_2)=NH_2{}^+$, wherein $R_{14}$ is an alkyl radical of, for example, from 1 to 10 carbon atoms, and cyclic amidinium cations such as 1,5-Diazabicyclo[5.4.0]undec-5-ene (DBU).

Alkali metal cations include lithium, sodium and potassium; and alkaline earth metal cations include magnesium, calcium, strontium and barium.

Preferred compounds of the formula I are those, in which

A is hydrogen, $C_1-C_4$-alkyl, triphenylmethyl, benzyl or a group

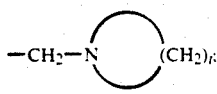

t is 4 or 5;
$R_1$ is hydrogen, fluorine or $C_1-C_4$-alkyl;
$R_2$ is hydrogen, a group

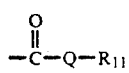

or a group

$R_3$ is hydrogen or $C_1-C_4$-alkyl;
$R_4$ is hydrogen or $C_1-C_4$-alkyl, or $R_3$ and $R_4$ together represent a chemical bond;
$R_5$ is hydrogen, $C_1-C_4$-alkyl, benzyl or an alkali metal, alkaline earth metal, ammonium, organic ammonium, trialkylsulphonium, trialkylsulfoxonium, phosphonium or amidinium cation;
$R_6$ is hydrogen, $C_1-C_4$-alkyl, benzyl or an alkali metal, alkaline earth metal, ammonium, organic ammonium, trialkylsulphonium, trialkylsulfoxonium, phosphonium or amidinium cation;
X is hydrogen or $C_1-C_4$-alkyl;
Y is hydrogen or $C_1-C_4$-alkyl or together with X a $-CH_2-(CH_2)_p-CH_2-$ group or together with Z a $C_1-C_4$-alkylene bridge which is substituted by $R_7$ and $R_8$;
Z is hydrogen or $C_1-C_4$-alkyl or together with X a $C_2-C_4$-alkylene bridge which is substituted by $R_7$ and $R_8$;
Q is oxygen, sulfur or $NR_{10}$;
$R_7$ is hydrogen, $C_1-C_4$-alkoxy or $C_1-C_4$-alkyl;
$R_8$ is hydrogen, $C_1-C_4$-alkoxy or $C_1-C_4$-alkyl;
$R_9$ is $C_1-C_6$-alkyl, $C_2-C_6$-alkenyl, $C_2-C_6$-alkynyl; or $C_1-C_6$-alkyl, $C_2-C_6$-alkenyl, $C_2-C_6$-alkynyl substituted by halogen or $C_1-C_4$-alkoxy; or phenyl, benzyl; or phenyl, benzyl substituted by $C_1-C_4$-alkyl, halogen, $C_1-C_4$-haloalkyl, $C_1-C_4$-alkoxy, cyano, nitro, $C_1-C_4$-alkoxycarbonyl or $S(O)_m-C_1-C_4$-alkyl;
$R_{10}$ is hydrogen, $C_1-C_6$-alkyl, $C_1-C_6$-alkoxy, $C_2-C_6$-alkenyl, $C_3-C_6$-alkynyl; or $C_1-C_6$-alkyl, $C_2-C_6$-alkenyl, $C_3-C_6$-alkynyl substituted by halogen or $C_1-C_4$-alkoxy;
$R_{11}$ is $C_1-C_6$-alkyl, $C_3-C_6$-alkenyl, $C_3-C_6$-alkynyl; or $C_1-C_6$-alkyl, $C_3-C_6$-alkenyl, $C_3-C_6$-alkynyl substituted by halogen or $C_1-C_4$-alkoxy; or phenyl, benzyl; or phenyl, benzyl substituted by $C_1-C_4$-alkyl, halogen, halomethyl, $C_1-C_4$-alkoxy, cyano, nitro, $C_1-C_4$-alkoxycarbonyl or $S(O)_n-C_1-C_4$-alkyl;
m is 0, 1 or 2;
n is 0, 1 or 2;
p is 1 or 2;
with the proviso that $R_1$, $R_2$, $R_3$, $R_4$, X, Y and Z are not simultaneously hydrogen; and if $R_1$, $R_3$, $R_4$, X, Y and Z are simultaneously hydrogen, $R_9$ is not methyl.

Further preferred compounds of the formula I are those in which
A is hydrogen, triphenylmethyl, benzyl or a group

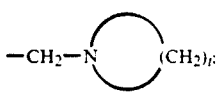

$R_2$ is hydrogen or a group

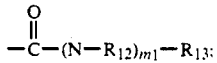

$R_{12}$ is hydrogen or $C_1-C_4$-alkyl;
$m_1$ is 0 or 1;
$R_{13}$ is $C_1-C_4$-alkyl, methoxy, trifluoromethyl, phenyl, benzyl, phenyl substituted by halogen or methoxy; or benzyl substituted by halogen, methoxy, methylthio, cyano or trifluoromethyl.

Preferred compounds of the formula I which must be emphasised are those in which
A is hydrogen;
$R_5$ is hydrogen or an alkali metal, alkaline earth metal, ammonium, organic ammonium, trialkylsulphonium, trialkylsulfoxonium, phosphonium or amidinium cation; and
$R_6$ is hydrogen or an alkali metal, alkaline earth metal, ammonium, organic ammonium, trialkylsulphonium, trialkylsulfoxonium, phosphonium or amidinium cation.

Further preferred compounds from amongst those of the formula I are those in which $R_1$ and A are hydrogen.

Furthermore, compounds amongst those of the formula I which are of particular interest are those in which $R_2$ and A are hydrogen.

Furthermore, compounds amongst those of the formula I which are preferred are compounds of the formulae

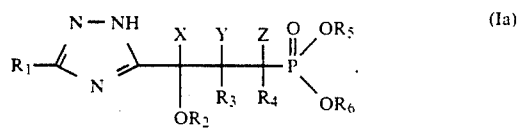

wherein $R_1$, $R_2$, $R_3$, $R_4$, $R_5$, $R_6$, X, Y and Z have the meaning given under formula I, especially preferred are those compounds, wherein $R_1$ is hydrogen or methyl; $R_2$ is hydrogen or acetyl; $R_3$ is hydrogen or methyl; $R_4$ is hydrogen or methyl; $R_5$ is hydrogen or ethyl; $R_6$ is hydrogen or ethyl; X is methyl, ethyl or isopropyl; Y is hydrogen or methyl; and Z is hydrogen, methyl or ethyl;

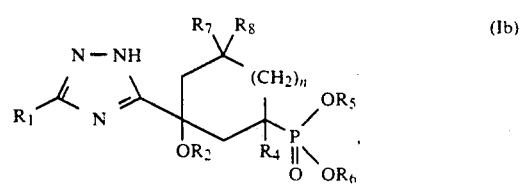

wherein $R_1$, $R_2$, $R_4$, $R_5$, $R_6$, $R_7$ and $R_8$ have the meaning given under formula I and n is 0, 1 or 2, especially preferred are those compounds, wherein $R_1$ is hydrogen or methyl; $R_2$ is hydrogen, acetyl or N-phenyl carbamoyl; n is 0 or 1; $R_4$ is hydrogen or methyl; $R_5$ is hydrogen, ethyl or benzyl; $R_6$ is hydrogen, ethyl or benzyl; $R_7$ is hydrogen or methyl; and $R_8$ is hydrogen or methyl;

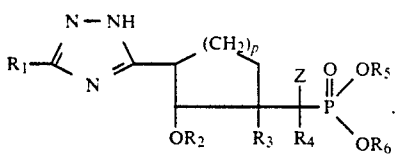

wherein $R_1$, $R_2$, $R_3$, $R_4$, $R_5$, $R_6$, Z and p have the meaning given under formula I, especially preferred are those compounds, wherein $R_1$, $R_2$, $R_3$, $R_4$, $R_5$, $R_6$ and Z each is hydrogen and p is 1 or 2;

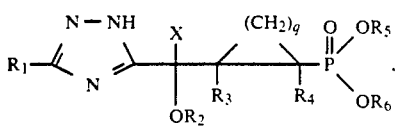

wherein $R_1$, $R_2$, $R_3$, $R_4$, $R_5$, $R_6$ and X have the meanings given under formula I and q is 1, 2, 3 or 4, especially preferred are those compounds, wherein $R_1$, $R_2$, $R_3$, $R_4$, $R_5$ and $R_6$ each is hydrogen; X is hydrogen or methyl; and q is 1, 2, 3 or 4.

From within the scope of the formula I, mention must be made of trans-3-hydroxy-3-(1,2,4-triazole-3-yl)-cyclohexyl-phosphonic acid as a particularly preferred single compound.

A further subject of the present invention is a process for the preparation of compounds of the formula I which comprises reacting a compound of the formula II

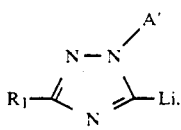

wherein A' is $C_1$-$C_4$-alkyl, $C_1$-$C_4$-alkenyl, triphenylmethyl, benzyl, a group

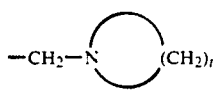

or $C_1$-$C_4$-alkyl substituted by hydroxy or $C_1$-$C_4$-alkoxy; and $R_1$ has the given meaning, with aldehydes or ketones of the formula III

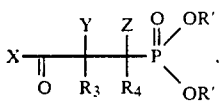

wherein $R_3$, $R_4$, X, Y and Z have the above given meaning and R' is $C_1$-$C_4$alkyl or benzyl, with the proviso that $R_3$ is hydrogen or $C_1$-$C_4$-alkyl, $R_4$ is hydrogen or $C_1$-$C_4$-alkyl, Y is hydrogen or $C_1$-$C_4$-alkyl, Z is hydrogen or $C_1$-$C_4$-alkyl, to give a compound of the formula Ia'

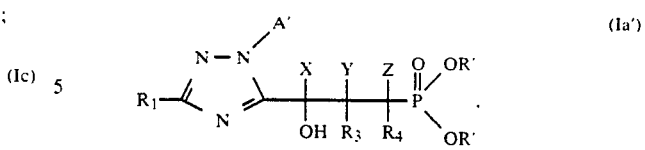

wherein A', $R_1$, $R_3$, $R_4$, R', X, Y and Z have the given meaning and optionally cleaving protecting groups A' and/or R' and further converting them into a salt.

Said reaction is carried out in a manner or analogously as given by A. R. Katritzky, Tetrahedron 46 (1990), page 641 ff.

Compounds of formula II are well known and for instance are prepared by reacting a 1,2,4-triazole in an organic solvent, especially tetrahydrofuran or diethylether, in the presence of n-butyl lithium at temperatures between −50° to −90° C.

Compounds of formula III are well known and can for instance be prepared in a manner given in Houben-Weyl, 4th Edition, volume XII/1, pages 463 ff; and Houben-Weyl, 4th Edition, volume E2, pages 352 ff.

Compounds of the formula I, wherein $R_3$ and $R_4$ together represent a chemical bond or Y together with Z represent a $C_1$-$C_4$-alkylene bridge can be prepared according to the following reaction schemes ("Tr" is the triphenylmethyl group):

Synthesis of Compound 1.012

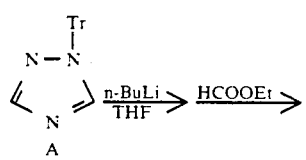

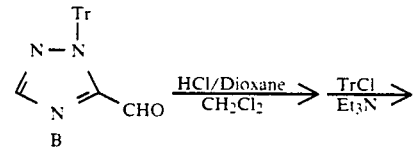

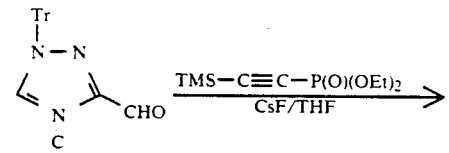

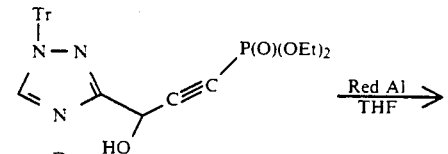

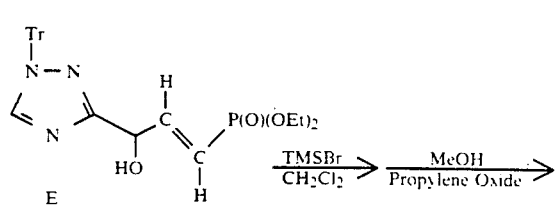

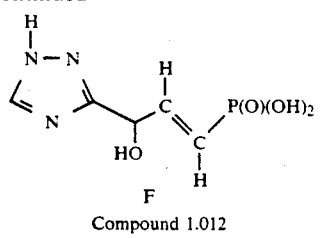
Compound 1.012

Synthesis of Compound 4.001

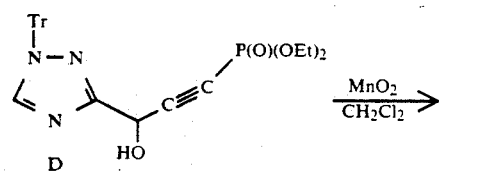

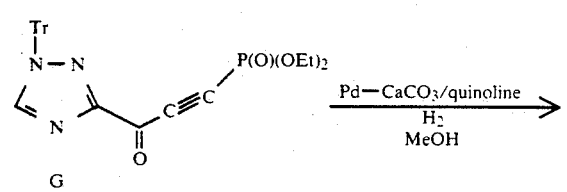

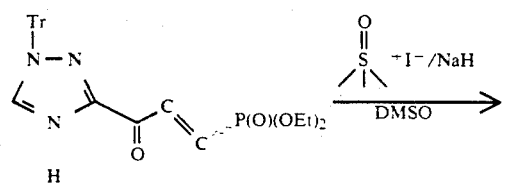

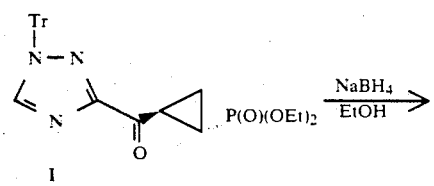

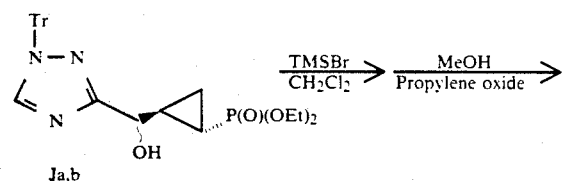

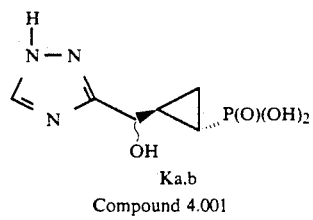
Compound 4.001

Compounds of formula I, wherein $R_5$ and $R_6$ are hydrogen for instance are prepared by treating a compound of formula Ia''

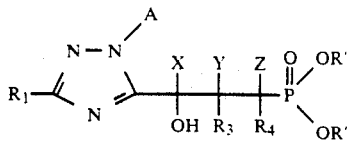 (Ia'')

with an acid or a halosilane to obtain a compound of the formula Ia'''

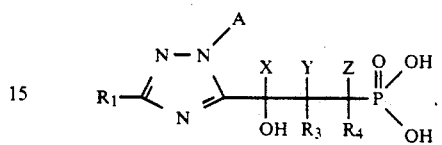 (Ia''')

wherein A, R', $R_1$, $R_3$, $R_4$, X, Y and Z have the meaning given above.

The reaction is carried out in an organic solvent, especially $CH_2Cl_2$, at temperatures between 10° and 50° C., especially in a manner or analogously as given by T. Morita, Bull. Chem. Soc. Japan 51 (1978), page 2169 ff.

The protecting groups A as triphenylmethyl, benzyl or a group

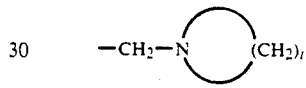

can be cleaved a) under acidic or reductive conditions for the triphenylmethyl group, b) by hydrogenolysis with palladium active charcoal or by reductive cleavage by sodium in liquid ammonia for the benzyl group, or c) by cleavage with $NaBH_4$ for the group

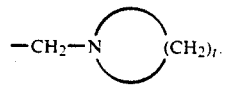

Said reactions are carried out in a manner or analogously as given by D. K. Anderson, Heterocyclic Chemistry 23 (1986), pages 1257ff; and A. R. Katritzky, Tetrahedron 46 (1990), page 641 ff.

The cleavage of protecting groups for A as triphenylmethyl; $R_5$ as $C_1$-$C_4$-alkyl, benzyl or an alkali metal, alkaline earth metal, ammonium, organic ammonium, trialkylsulphonium, trialkylsulfoxonium, phosphonium or amidinium cation and $R_6$ as $C_1$-$C_4$-alkyl, benzyl or an alkali metal, alkaline earth metal, ammonium, organic ammonium, trialkylsulphonium, trialkylsulfoxonium, phosphonium or amidinium cation can be done sequentially or in a one step process according to the following scheme

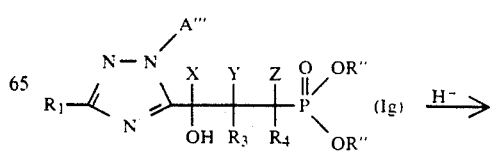 (Ig)

-continued

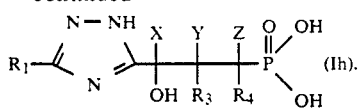
(Ih).

wherein $R_1$, $R_3$, $R_4$, X, Y and Z have the given meaning, A''' is triphenylmethyl and R'' is $C_1$-$C_4$-alkyl, benzyl or an alkali metal, alkaline earth metal, ammonium, organic ammonium, trialkylsulphonium, trialkylsulfoxonium, phosphonium or amidinium cation.

The reaction is carried out without solvent at temperatures between 10° and 50° C. in the presence of an organic or inorganic acid, for example HCl or HBr.

Said type of reaction is well known in the art.

Compounds of the formula I, wherein $R_5$ and $R_6$ are benzyl are prepared by reacting the free phosphonic acid compound Ib' with O-benzyl-N,N'-dicyclohexylisourea according to the following scheme

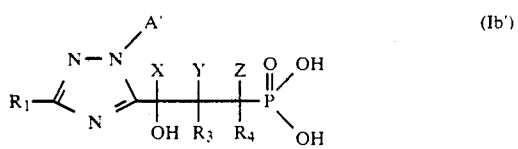
(Ib')

with 2 equivalents of O-benzyl-N,N'-dicyclohexylisourea of the formula

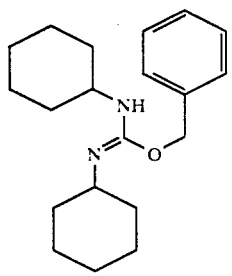
(V)

to give the compound of the formula

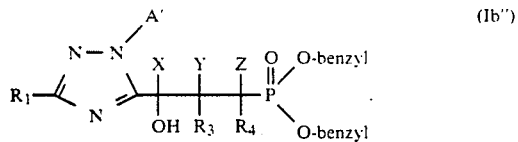
(Ib'')

The reaction is carried out under reflux in an organic solvent such as benzene or toluene or dimethylformamide; for example in a manner or analogously as given by M. Hoffmann, Synthesis 1988, page 62 ff.

Compounds of the formula I, wherein $R_2$ is a group

or a group

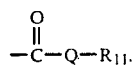

are prepared by reacting a compound of formula Ih with acid halides or anhydrides according to the following scheme

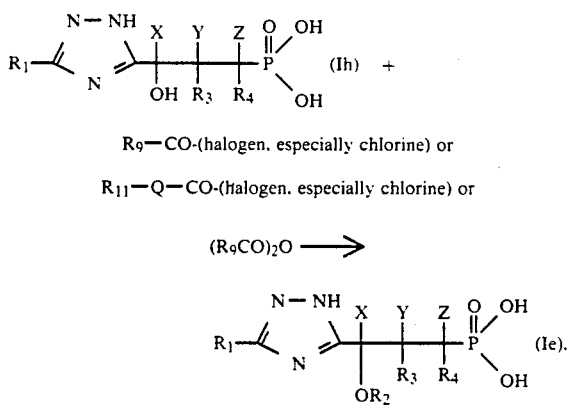

$R_9$—CO-(halogen, especially chlorine) or $R_{11}$—Q—CO-(halogen, especially chlorine) or $(R_9CO)_2O \longrightarrow$

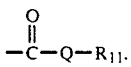
(Ie).

in which $R_2$ has the meanings given above except for hydrogen.

Said reaction is carried out in a manner or analogously as given in Chem Rev. 1953, 52, pages 237-416.

Compounds of the formula I, wherein $R_2$ is a group

in which Q is $NR_{10}$ and $R_{10}$ is hydrogen, are prepared by reacting a compound of formula Ih with isocyanates which lead to carbamates according to the following scheme

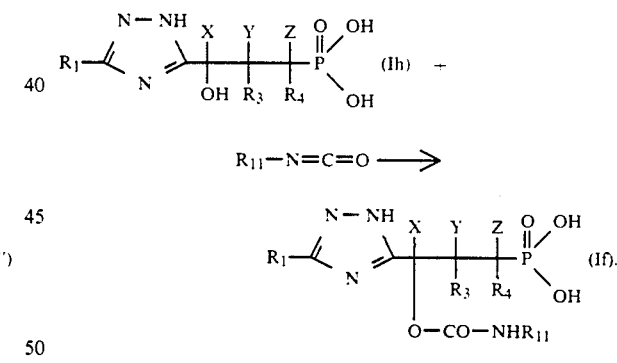

$R_{11}$—N=C=O $\longrightarrow$

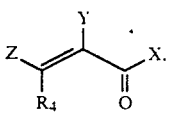
(If).

Said reaction is carried out in a manner or analogously as given by Satchell & Satchell, Chem. Soc. Rev, 4,231 (1975).

1) The ketophosphonates of formula III are prepared
a) by reacting a trialkylphosphite of the formula $P(OR')_3$ (VI)

with an enone of the formula (VII)

wherein R', Z, $R_4$, X and Y have the above given meaning.

Said reaction is carried out for example in an organic solvent such as phenol at a temperature between 50° and 100° C., especially in a manner or analogously as given by R. G. Harvey, Tetrahedron, 22 (1966), pages 2561 ff.

b) by addition of a dialkylphosphite to an enone according to the following scheme $$HPO(OR')_2 + Z\underset{R_4}{\overset{Y}{\diagdown}}C=C\underset{O}{\overset{}{\diagup}}X \quad (VII) \longrightarrow$$

$$X-\overset{Y}{\underset{O}{\overset{|}{C}}}-\overset{Z}{\underset{H}{\overset{|}{C}}}-\overset{O}{\underset{R_4}{\overset{\|}{P}}}\diagdown\overset{OR'}{OR'} \quad (III').$$

wherein R', R$_4$, X, Y and Z have the given meaning.

The reaction is carried out in the presence of of an alkoxide, such as sodium ethoxide, at a temperature between 50° and 100° C. Said reaction can be carried out in a manner or analogously as given by Pudovic, Zhur Obsh. Khim. 27(1957) pages 1617 ff (CA 52, 3713 (1958).

c) by condensation of an aldimine of the formula $$Z\underset{R_4}{\overset{Y}{\diagdown}}C=C-CH=N-C(CH_3)_3 \quad (VIII)$$

with trialkylphosphite of the formula $$P(OR')_3$$

in the presence of formic acid and after hydrolysis to give compound of formula IIIa $$X'-\overset{Y}{\underset{O}{\overset{|}{C}}}-\overset{Z}{\underset{H}{\overset{|}{C}}}-\overset{O}{\underset{R_4}{\overset{\|}{P}}}\diagdown\overset{OR'}{OR'} \quad (IIIa)$$

wherein R', R$_4$, Y and Z have the given meaning and X' is hydrogen.

Said reaction is carried out in an alcohol, especially ethyl alcohol at a temperature between 10° and 50° C. in a manner or analogously as given by P. Savignac, Synthesis 1987, pages 1037 ff.

2) Vinylphosphonates of formula XI are prepared by reacting a) an acylphosphonate of the formula $$(R'O)_2\overset{O}{\overset{\|}{P}}-\overset{O}{\overset{\|}{C}}-Z \quad (IX)$$

with an enone of formula $$(Phenyl)_3P=CH-CO-X \quad (X)$$

to give a vinylphosphonate of the formula $$(R'O)_2\overset{}{\underset{O}{\overset{\|}{P}}}-\overset{}{\underset{Z}{\overset{|}{C}}}=CH-CO-X \quad (XI)$$

Said reaction is carried out in an organic solvent, especially in benzene or toluene at a temperature near the boiling point in a manner or analogously as given by E. Öhler, Monatshefte für Chemie 116(1)(1986), pages 77 ff.

b) β-chloroenones of the formula $$Z\underset{Cl}{\overset{}{\diagdown}}C=C\underset{}{\overset{O}{\diagup}}X \quad (XII)$$

with trialkylphosphite of the formula $$P(OR')_3$$

to give a vinylphosphonate of the formula XI.

Said reaction is carried out without solvent at temperatures between 100° and 150° C. in a manner or analogously as given by F. Hammerschmidt, Liebigs Ann. Chem. 1979, pages 492 ff.

Optionally the compounds of formula III, wherein R$_3$ is hydrogen can be alkylated with an alkylating agent, especially CH$_3$I or CH$_3$Br, in the presence of a base, such as lithium diisopropylamide, NaH, tert.-butyl-O-K$^+$ or DBU (1,8-diazabicyclo[5.4.0.]undec-7-ene) at temperatures between −78° and +50° C. according to known alkylating methods, especially alkylation of enamines or silyl enol ethers.

General reviews on 1,2,4-Triazoles is Polya, J. B. in Comprehensive Heterocyclic Chemistry, Potts, K. T. Ed.; Pergamon: Oxford, 1984, vol. 5, pages 733 ff.

The compounds of the formula I are employed in unaltered form, as obtainable by the synthesis, or preferably together with the auxiliaries conventionally used in formulation technology, and they are therefore processed in a known manner to give, for example, emulsifiable concentrates, directly sprayable or dilutable solutions, dilute emulsions, wettable powders, soluble powders, dusts, granules, and also encapsulations, for example in polymeric substances. The application methods, such as spraying, atomising, dusting, scattering or pouring, as well as the type of compositions are selected to suit the intended aims and the prevailing circumstances.

The formulations, i.e. the compositions, preparations or combinations comprising the active substance of the formula I and, if desired, one or more solid or liquid additives, are prepared in a known manner, for example by intimately mixing and/or grinding the active substances with extenders, for example with solvents, solid carriers and, if desired, surface-active compounds (surfactants).

The following are possible as solvents: aromatic hydrocarbons, in particular the fractions C$_8$ to C$_{12}$, such as mixtures of alkylbenzenes, for example xylene mixtures or alkylated naphthalenes; aliphatic and cycloaliphatic hydrocarbons such as paraffins, cyclohexane or tetrahydronaphthalene; alcohols, such as ethanol, propanol or butanol; glycols as well as their ethers and esters, such as propylene glycol or dipropylene glycol ether, ketones such as cyclohexanone, isophorone or diacetone alcohol, strongly polar solvents such as N-methyl-2-pyrrolidone, dimethyl sulfoxide or water; vegetable oils as well as their esters, such as rapeseed oil, castor oil or soybean oil; and if appropriate also silicone oils.

Suitable surface-active compounds are non-ionic, cationic and/or anionic surfactants having good emulsifying, dispersing and wetting properties, depending on the nature of the active substance of the formula I to be formulated. Surfactants are also to be understood as meaning mixtures of surfactants.

Anionic surfactants which are suitable can be either so-called water-soluble soaps or water-soluble synthetic surface-active compounds. Suitable soaps which may be mentioned are the alkali metal salts, alkaline earth metal salts or substituted or unsubstituted ammonium salts of higher fatty acids ($C_{10}$–$C_{22}$), such as the Na salts or K salts of oleic or stearic acid, or of natural mixtures of fatty acids which can be obtained, for example, from coconut oil or tallow oil. Mention must also be made of the fatty acid methyltaurinates.

However, so-called synthetic surfactants are used more frequently, in particular fatty alcohol sulfonates, fatty alcohol sulfates, sulfonated benzimidazole derivatives or alkylarylsulfonates.

The fatty alcohol sulfonates or fatty alcohol sulfates are generally in the form of alkali metal salts, alkaline earth metal salts or substituted or unsubstituted ammonium salts, and have an alkyl radical having 8 to 22 C atoms, alkyl also including the alkyl moiety of acyl radicals, for example the Na or Ca salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and one fatty acid radical having 8 to 22 C atoms. Examples of alkylarylsulfonates are the Na, Ca or triethanolamine salts of dodecylbenzenesulfonic acid, of dibutylnaphthalenesulfonic acid or of a naphthalenesulfonic acid/formaldehyde condensation product.

Other suitable compounds are the corresponding phosphates, such as the salts of the phosphoric ester of a p-nonylphenol/(4–14)-ethylene oxide adduct, or phospholipids.

Suitable non-ionic surfactants are mainly polyglycol ether derivatives of aliphatic or cycloaliphatic alcohols, of saturated or unsaturated fatty acids and of alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other non-ionic surfactants which are suitable are the water-soluble polyethylene oxide adducts with polypropylene glycol, ethylenediaminopolypropylene glycol and alkylpolypropylene glycol which have 1 to 10 carbon atoms in the alkyl chain and which contain 20 to 250 ethylene glycol ether groups and 10 to 100 propylene glycol ether groups. The abovementioned compounds customarily contain 1 to 5 ethylene glycol units per propylene glycol unit.

Examples of non-ionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Other suitable substances are fatty acid esters of polyoxyethylenesorbitan, such as polyoxyethylenesorbitan trioleate.

The cationic surfactants are mainly quaternary ammonium salts, which contain at least one alkyl radical having 8 to 22 C atoms as N-substituents and which have lower halogenated or free alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants customary in formulation technology are described, inter alia, in the following publications:
"McCutcheon's Detergents and Emulsifiers Annual", Mc Publishing Corp., Glen Rock, N.J., 1988;
M. and J. Ash, "Encyclopedia of Surfactants", Vol. I–III, Chemical Publishing Co., N.Y., 1980–1981.
Dr. Helmut Stache, "Tensid-Taschenbuch [Surfactant Guide]", Carl Hanser Verlag, Munich, Vienna, 1981;

As a rule, the pesticidal preparations contain 0.1 to 99%, in particular 0.1 to 95%, of the active substance of the formula I, 1 to 99% of a solid or liquid additive and 0 to 25%, in particular 0.1 to 25%, of a surfactant.

While concentrated compositions are more preferred as commercial goods, the user generally uses dilute compositions.

The compositions can also comprise further additives such as stabilisers, for example epoxidised or unepoxidised vegetable oils (epoxidised coconut oil, rapeseed oil or soybean oil), defoamers, for example silicone oil, preservatives, viscosity regulators, binders, tackifiers, as well as fertilisers or other active substances for achieving specific effects.

In particular, preferred formulations have the following composition: (%=percent by weight)

| Emulsifiable concentrates: | |
|---|---|
| Active ingredient: | 1 to 90%, preferably 5 to 20% |
| Surface-active agent: | 1 to 30%, preferably 10 to 20% |
| Liquid carrier: | 50 to 94%, preferably 70 to 85% |
| Suspension concentrates: | |
| Active ingredient: | 5 to 75%, preferably 10 to 50% |
| Water: | 94 to 24%, preferably 88 to 30% |
| Surface-active agent: | 1 to 40%, preferably 2 to 30% |

As a rule, the active substances of the formula I are sucessfully employed at application rates from 0.001 to 10 kg/ha, in particular 0.005 to 2 kg/ha. The dosage rate which is required for the desired action can be determined by tests. It depends on the nature of the action, the development stage of the crop plant and the weed, as well as on the application (location, time, method) and, due to these parameters, can vary within wide limits.

Controlled release of active substance

The dissolved active substance is applied to mineral granule carriers or polymerised granules (urea/formaldehyde) and allowed to dry. If desired, a coating can be applied (coated granules), which permits slow release of the active substance over a certain period.

The following examples are intended to illustrate the invention in greater detail.

A. Preparation of compounds of formula I
The preparation follows the following scheme

(Ph₃CCl = triphenylmethylchloride;
Et₃N = triethylamine;
DMF = dimethylformamide)

-continued

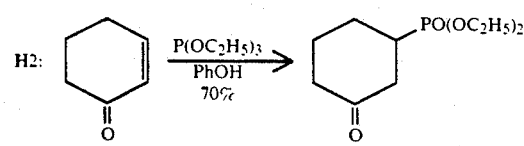

(P(OC₂H₅)₃ = triethylphosphite;
PhOH = phenol)

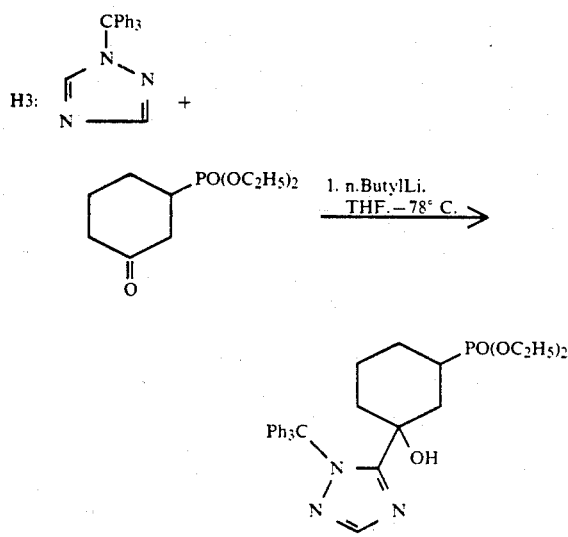

(THF = tetrahydrofuran)

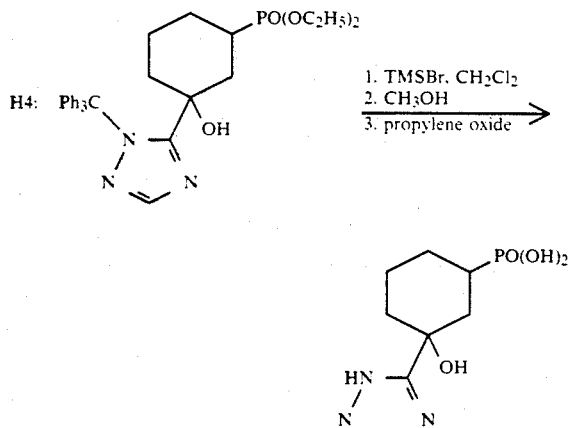

(TMSBr = trimethylsilylbromide)

EXAMPLE H1

To a mixture of 1H-1,2,4-triazole (75 g, 1.09 mol) and triphenylmethylchloride (302.7 g, 1.09 mol) in 1200 mL of dimethylformamide was added triethylamine (182 mL, 1.30 mol) dropwise with cooling in an ice bath. After completion of the addition, the mixture was allowed to warm to room temperature and stirred overnight. To the mixture, 1.5 L of water was added in 1.5 h. The precipitates were collected on a glass filter, washed with water (5×250 mL) and with ether (5×250 mL), and dried in vacuo to give 342 g (quant) of the compound of the formula

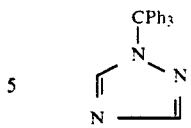

as slightly yellowish solid.

$^1$H NMR (90 MHz, CDCl₃) δ 8.07 (s, 1), 8.03 (s, 1), 6.95-7.49 (m, 15).

EXAMPLE H2

This compound was prepared according to the procedure described by Johnson. (Crooks, S. L.; Robinson, M. B.; Koerner, J. F.; Johnson, R. L. J. Med. Chem. 1986, 29, 1988-1995).

To a solution of 2-cyclohexen-1-one (25 mL, 0.26 mol) in 64.6 g of warm phenol (ca. 50° C.) was added triethyl phosphite (56.8 mL, 0.32 mol) over 10 min via syringe. The temperature was maintained at 100° C. for 24 h with an oil bath. Most of the remaining phenol was removed under reduced pressure (8 mmHg) at 50° C. Distillation at 133°-139° C. (0.3 mmHg) gave 42.6 g (70% yield) of the compound of the formula

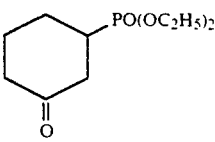

$^1$H NMR (90 MHz, CDCl₃) δ 3.95-4.27 (quintet, 4, J=7.3), 1.45-2.49 (m, 9), 1.24-1.40 (t, 6, J=7.0).

EXAMPLE H3

A clear solution of the compound obtained in Examples H1 (10 g, 32 mmol) in 150 mL of warm tetrahydrofuran was cooled to −78° C. n-Butyllithium (38.4 mmol, in 1.5 M hexane) was added dropwise in 10 minutes and was stirred for 50 minutes at −78° C. n-Butyllithium has to be added before precipitation of the compound obtained in Example H1 starts. To the resulting reddish (sometimes yellow) solution was added the compound obtained in Example H2 (9.03 g, 38.4 mmol) and stirred for 1 h. The reaction was quenched with 50 mL of saturated aqueous ammonium chloride and was allowed to warm to room temperature. The mixture was diluted with 100 mL of water, extracted with chloroform, dried over MgSO₄, and concentrated. Column chromatography on silica gel (400 g) with ethyl acetate then ethyl acetate/ethanol (20:1) gave 9.85 g (57% yield) of the compound of the formula

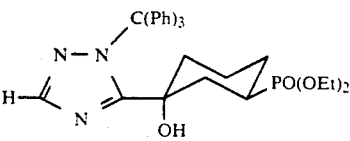

as a colorless solid.

$^1$H NMR (90 MHz, CDCl₃) δ 7.85 (s, 1), 7.10-7.31 (m, 15), 3.85-4.17 (quintet, 4, J=7.4), 0.80-2.30 (m, 9), 1.20-1.36 (t, 6, J=7.2).

EXAMPLE H4

To a solution of the compound obtained according to Example H3 (6.0 g 11.0 mmol) in 150 mL of CH2Cl2 was added trimethylsily bromide (7.27 mL, 55.0 mmol) in one portion and the mixture was stirred overnight at room temperature. After addition of methanol (75 mL) the mixture was stirred for 1 h at room temperature. Propylene oxide (15 mL) was added and the resulting mixture was stirred for another 1 h. Slow addition of 600 mL of ether caused precipitation of the desired compound. The precipitates were collected on a glass filter under a stream of nitrogen, washed 5 times with 50 mL of ether, and dried in vacuo to give 2.62 g (96% yield) of trans-3-hydroxy-3-(1,2,4-triazole-3-yl)-cyclohexanephosphonic acid (compound no. 2.002) of the formula

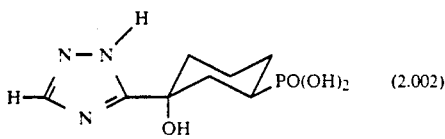

mp 166° C. decomp.

$^1$H NMR (90 MHz, D$_2$O) δ 8.80 (s, 1H), 1.1-2.5 (m, 9H).

EXAMPLE H5 a) To a solution of 1-methyl-1,2,4-triazole (3.0 g, 36.1 mmol) in tetrahydrofurane (60 ml) was added n-buthyl-lithium (43.3 mmol, 1.2 eq) at −78° C. under nitrogen. The mixture was stirred for 1 hour, then diethyl 3-oxo-butylphosphonate (8.3 g, 39.7 mmol, 1.1 eq) was added. The mixture was stirred for 2 hours and quenched with aq. NH4Cl (ca. 15 ml). The mixture was warmed to room temperature and extracted with CH2Cl2 (5×100 ml). The extract was dried over MgSO4, concentrated in vacuo, and purified by a silica gel column chromatography (200 g, AcOEt-EtOH) to give (2.99 g, 28% yield) of diethyl 3-hydroxy-3-methyl-3-(1-methyl-1,2,4-triazol-5-yl)propyl-phosphonate.

$^1$H NMR (90 MHz, CDCl$_3$) δ 7.75 (s, 1H), 4.13 (s, 3H), 4.29-3.90 (m, 4H), 2.80-1.80 (m, 5H), 1.63 (s, 3H), 1.37 (t, 3H, J=7.0 Hz), 1.33 (t, 3H, J=7.0 Hz).

b) To a solution of diethyl 3-hydroxy-3-methyl-3-(1-methyl-1,2,4-triazol-5-yl)propylphosphonate (1.2 g, 4.12 mmol) in CH2Cl2 (24 ml) was added TMSBr (2.72 ml, 20.6 mmol, 5 eq) at room temperature under nitrogen. The reaction mixture was stirred for 16 hours. Then methanol (12 ml) was added to the mixture. After stirring for 2 hours, addition of propylene oxide (2.4 ml) and dilution with diethylether gave colourless precipitates which were collected on a glass filter under nitrogen, washed with diethylether, and dried in vacuo to give pure 3-hydroxy-3-methyl-3-(1-methyl-1,2,4-triazol-5-yl)propyl-phosphonic acid, compound no 5.001 (0,63 g, 65% yield).

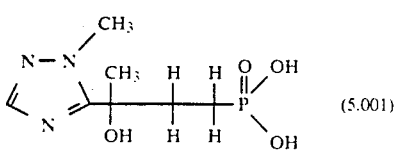

$^1$H NMR (90 MHz, D$_2$O) δ 8.31 (s, 1H), 4.16 (s, 3H), 2.37-1.48 (m, 4H), 1.72 (s, 3H), melting point 188°-191° C.

1-methyl-1,2,4-triazole was prepared according to the procedure by Dallacher and Minn, Chemiker-Zeitung 1986, 110, 101-108.

In the following examples the substituent "Tr" is triphenylmethyl.

EXAMPLE H6: PREPARATION OF COMPOUND 1.012:

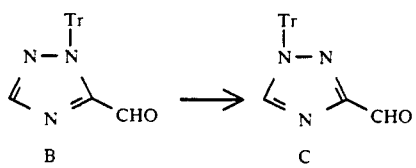

To a solution of Triazolecarbaldehyde B (73.7 g, 0.217 mol) in 1 l of CH2Cl2 was added 4N HCl in dioxane (59.7 mL, 0.239 mol) at room temperature and the mixture was stirred for 30 min. Tritylchloride (6.05 g 0.0217 mol) and triethylamine (54.4 ml, 0.326 mol) were then added to this mixture at 0° C. and stirred at room temperature for 1 h. The reaction was quenched with water and extracted with CH2Cl2. Combined organic layers were dried over MgSO4, concentrated in vacuo, and triturated with ether to give triazolecarbaldehyde C (69.0 g, 94%) as a colorless powder.

$^1$H NMR (90 MHz, CDCl$_3$) δ 10.04 (s, 1H), 8.13 (s, 1H), 7.47-6.98 (m, 15H).

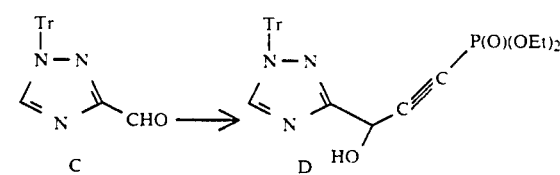

To a stirred solution of diethyl 2-(trimethylsilyl)ethynylphosphonate (0.234 g, 1.0 mmol) and triazolecarbaldehyde C (0.341 g, 1.0 mmol) in 5 ml of THF was added cesium fluoride (0.055 g, 0.36 mmol) at 0° C. and the mixture was stirred for 3 h at the same temperature. The reaction was quenched with aq. NH4Cl, extracted with CH2Cl2, dried over MgSO4, and concentrated in vacuo. The resulting crude material was purified by silica gel chromatography (ethyl acetate:CH2Cl2=9:1) to give D (0.233 g, 46%) as colorless solid: m.p. 155°-157° C.

$^1$H NMR (90 MHz, CDCl$_3$) δ 7.98 (s, 1H), 7.48-6,95 (m, 15H), 5.69 (dd, 1H, J=8.3 Hz, 3.8 Hz), 4.49 (bd, 1H, J=8.3 Hz), 4.08 (quintet, 4H, J=7.3 Hz), 1.27 (t, 6H, J=7.0 Hz).

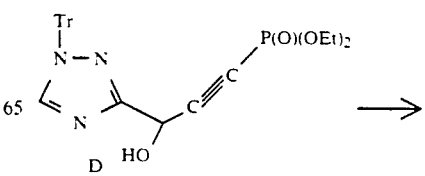

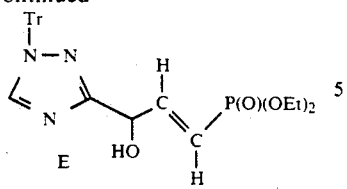

A solution of RedAl (0.29 ml, 3.4M in toluene, 1.0 mmol) in THF (3 ml) was added dropwise to a stirred solution of D (0.502 g, 1.0 mmol) in THF (5 ml) at −78° C. After stirring for 30 min at −78° C., the mixture was warmed to room temperature and stirred further for 10 min. The reaction was quenched by addition of aq. NH$_4$Cl and diluted with CHCl$_3$. The mixture was stirred for 24 h at room temperature and extracted with CHCl$_3$, dried over MgSO$_4$, and purified by silica gel chromatography (ethyl acetate:ethanol=1:0-9:1) to give allyl alcohol E (0.165 g, 33%) as a colorless solid: m.p. 118°-122° C.

$^1$H NMR (90 MHz, CDCl$_3$) δ 7.94 (s, 1H), 7.45-6.77 (m, 16H), 6.10 (ddd, 1H, J=20.0 Hz, 16.9 Hz, 1.8 Hz), 5.63-5.39 (bs, 1H), 4.05 (m, 4H), 1.30 (t, 6H, J=7.0 Hz).

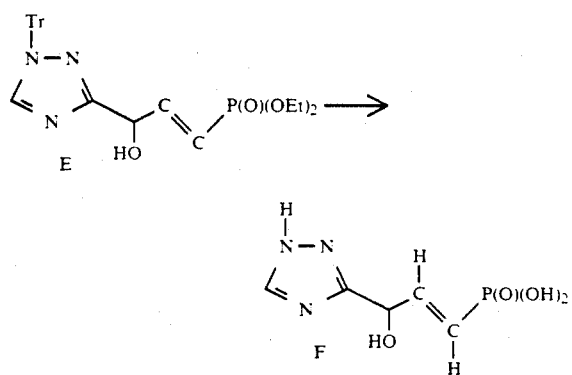

To a solution of allylalcohol E (0.374 g, 0.74 mmol) in CH$_2$Cl$_2$ (4 ml) was added TMSBr (0.4 ml, 3.0 mmol) at room temperature. After the mixture was stirred overnight at room temperature, methanol (0.4 ml) was added and the mixture was stirred for additional 1 h. Propylene oxide (0.4 ml) was added and the resulting suspension was stirred for 2 h at room temperature. Ether was added to complete precipitation and the precipitate were collected and washed with ether to give pure F (Compound 1.012, 0.152 g, quant.) as a colorless solid.

$^1$H NMR (90 MHz, D$_2$O) δ 8.92 (s, 1H), 5.70 (m, 1H), 6.93-6.05 (m, 2H).

EXAMPLE H7: PREPARATION OF COMPOUND 4.001:

To a well stirred solution of D (0.850 g, 1.7 mmol) in CH$_2$Cl$_2$ (15 ml), manganese oxide (1.14 g, 13.1 mmol) was added at room temperature. After vigorous stirring for 2 h, additional manganese oxide (0.50 g, 5.8 mmol) was added at room temperature and the mixture was stirred further for 1 h. The reaction mixture was filtered through a silica gel column with CH$_2$Cl$_2$ and ethyl acetate to give pure G (0.675 g, 79%) as a colorless solid: m.p. 95°-101° C.

$^1$H NMR (90 MHz, CDCl$_3$) δ 8.09 (s, 1H), 7.47-6.98 (m, 15H), 4.13 (m, 4H), 1.26 (t, 6H, J=7.0 Hz).

To a solution of G (3.0 g, 6.0 mmol) in methanol (30 ml) were added Pd on CaCO$_3$ (0.50 g) and quinoline (12 drops). The mixture was stirred under hydrogen atmosphere at room temperature for 7 h. The catalyst was filtered and washed with methanol and the filtrate was concentrated in vacuo. The residue was purified by column chromatography on silica gel (hexane:ethyl acetate=2:3-0:1) to give cis-H (0.60 g, 20%) and trans-H (0.83 g, 28%) in the order of elution.

cis-H:
m.p. 89°-92° C.
$^1$H NMR (90 MHz, CDCl$_3$) δ 8.06 (s, 1H), 7.92-7.05 (m, 16H), 6.28 (dd, 1H, J=13.8 Hz), 4.20 (m, 4H), 1.28 (t, 6H, J=7.0 Hz).

trans-H:
m.p. 105°-110° C.
$^1$H NMR (90 MHz, CDCl$_3$) δ 8.11 (s, 1H9, 8.08-6.88 (m, 17H), 4.20 (quintet, 4H, J=7.3 Hz), 1.30 (t, 6H, J=7.0 Hz).

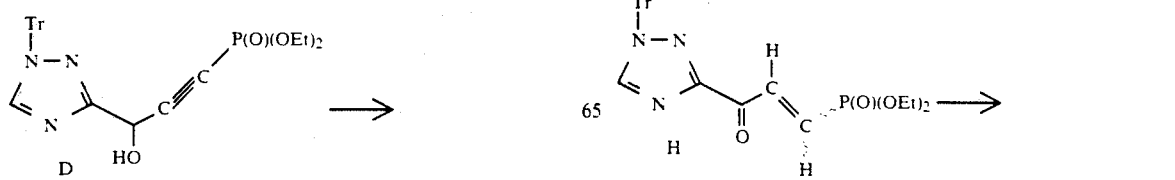

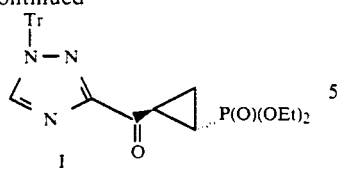

To a stirred mixture of sodium hydride (0.025 g, 60% in oil, 0.63 mmol) and trimethyloxosulfonium iodide (0.145 g, 0.65 mmol) was added DMSO (1 ml) slowly at room temperature and the mixture was stirred for 20 min at the same temperature. The resulting mixture of dimethyloxosulfonium methylylide was then added to a solution of cis-H (0.300 g, 0.6 mmol) in DMSO (1 ml) at room temperature. After stirring for 40 min, the reaction was quenched with aq. NH$_4$Cl. The mixture was extracted with ethyl acetate, dried over MgSO$_4$, and purified by silica gel chromatography (hexane:ethyl acetate:CH$_2$Cl$_2$ = 1:8:1) to give pure I (0.040 g, 13%) as a colorless solid: m.p.: 135°-138° C.

I was also obtained from trans-H in a 15% yield by the same method as above.

$^1$H NMR (90 MHz, CDCl$_3$) δ 8.08 (s, 1H), 7.46-6.95 (m, 15H), 4.27-3.83 (m, 4H), 3.77-3.28 (m, 1H), 1.95-1.08 (m, 9H).

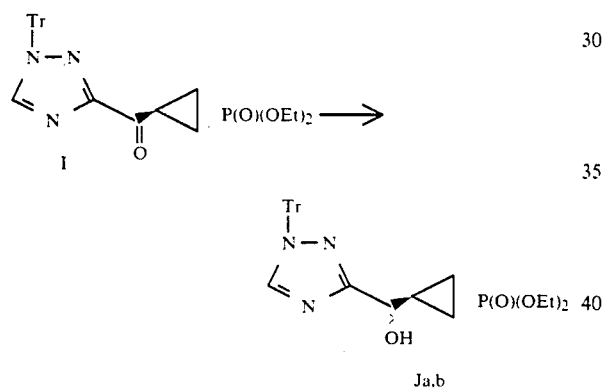

Sodium borohydride (0.005 g, 0.13 mmol) was added to a solution of I (0.130 g, 0.25 mmol) in ethanol (2 ml) at room temperature and the mixture was stirred for 2 h. The reaction was quenched with brine and the mixture was extracted with ethyl acetate, dried over MgSO$_4$ and purified by medium pressure liquid chromatography on silica gel (ethyl acetate:ethanol = 39:1-19:1) to give Ja (0.046 g, 36%) and Jb (0.043 g, 33%) in the order elution.

Ja: $^1$H NMR (90 MHz, CDCl$_3$) δ 7.92 (s, 1H), 7.42-7.05 (m, 15H), 4.58 (d, 1H, J=6.3 Hz), 4.24-3.88 (m, 4H), 3.21 (br, 1H), 2.30-0.90 (m, 10H).

Jb: $^1$H NMR (90 MHz, CDCl$_3$) δ 7.92 (s, 1H), 7.40-7.04 (m, 15H), 4.80 (br, 1H), 4.26-3.85 (m, 4H), 3.25 (br, 1H), 2.29-0.89 (m, 10H).

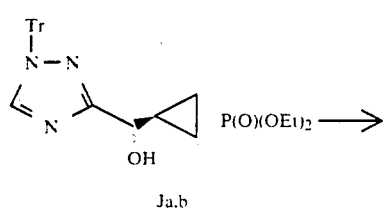

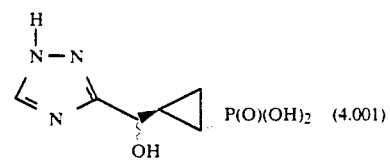

TMSBr (0.05 ml, 0.35 mmol) was added to a solution of Ja (0.046 g, 0.09 mmol, one isomer) in CH$_2$Cl$_2$ (0.5 ml) at room temperature and the mixture was stirred for 4 h. Additional TMSBr (0.02 ml, 0.15 mmol) was added and the mixture was stirred further for 1.5 h at room temperature and ether was added to complete precipitation. The precipitates were collected and washed with ether to give pure Ka (0.02 g, quant.) as a colorless solid.

Ka: $^1$H NMR (90 MHz, D$_2$O) δ 8.85 (s, 1H), 4.65 d, 1H, J=8.9 Hz), 2.30-0.95 (m, 4H).

Compound Jb was similarly deprotected to give a quantitative yield of Kb as a colorless solid.

Kb: $^1$H NMR (90 MHz, D$_2$O) δ 8.87 (s, 1H), 4.61 (d, 1H, J=8.1 Hz), 1.98-090 (m, 4H).

EXAMPLE H8: PREPARATION OF COMPOUND 1.056

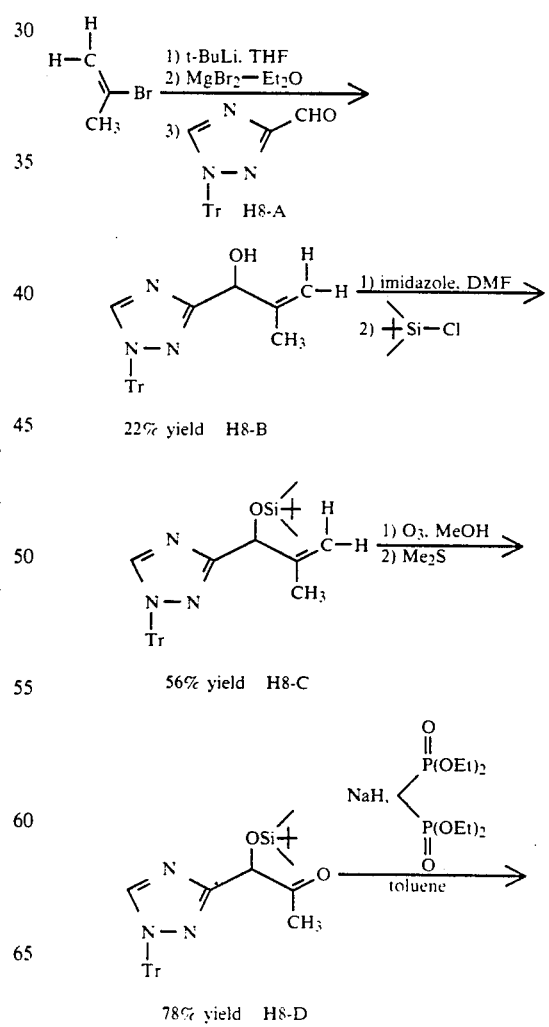

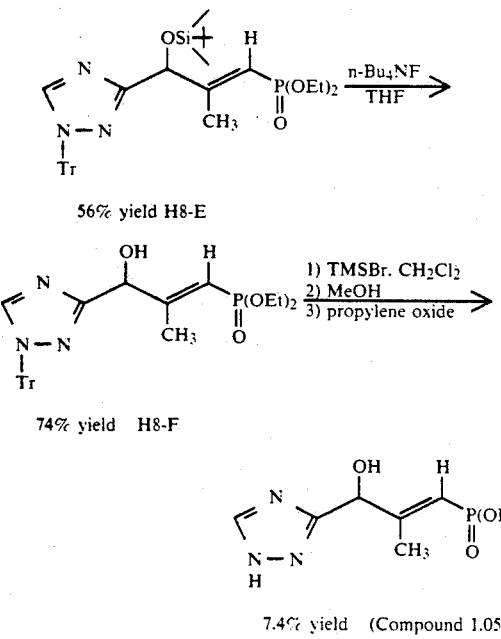

56% yield H8-E

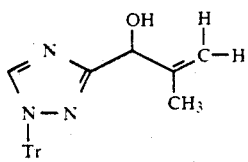

74% yield H8-F

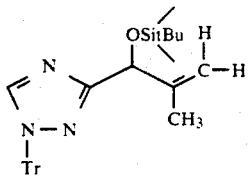

7.4% yield (Compound 1.056)

a) Preparation of compound H8-B:

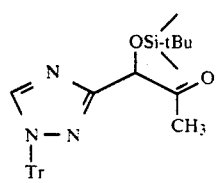
(H8-B)

To a solution of 2-bromopropene (7.32 g, 60.5 mmol) in 450 ml of THF was added t-BuLi (74.7 ml, 1.7 m in pentane, 127.1 mmol) under nitrogen at −78° C. After 1 h, MgBr$_2$.Et$_2$O (17.19 g, 66.6 mmol) was added to the mixture in one portion, then the mixture was allowed to warm to 0° C. and stirred for 1 h. Aldehyde H8-A (24.6 g, 72.6 mmol) was added to the mixture and stirred at 0° C. for 1.5 h. The reaction was quenched by addition of aq. NH$_4$Cl (40 ml), diluted with water, and extracted with CH$_2$Cl$_2$ (5×300 ml). The combined organic layers were dried over MgSO$_4$, concentrated, and purified by silica gel chromatography (AcOEt:CH$_2$Cl$_2$=1:5) t give 5.08 g (22% yield) of YK-79 as a colorless solid.

mp 111°-112° C.;
$^1$HNMR (90 MHz, CDCl$_3$) δ 7.90 (s,1), 7.40-7.05 (m,15), 5.32-5.15 (m,2), 5.01-4.94 (m,1), 2.98 (d,1,J=6.8), 1.65 (d,3,J=3.3).

b) Preparation of compound H8-C:

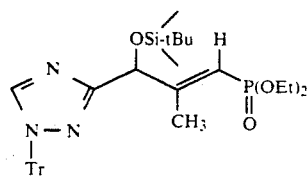
(H8-C)

To a solution of compound H8-B (7.30 g, 19.1 mmol) in 100 ml of DMF was added imidazole (1.95 g, 28.7 mmol) at room temperature under nitrogen. The mixture was cooled to 0° C. and t-butyldimethylsilyl chloride (3.17 g, 21.05 mmol) was added. After 30 min, the mixture was allowed to warm to room temperature and stirred for 18 h. Ice water was added to the mixture and extracted with AcOEt (4×100 ml). The combined organic layers were washed with water (6×100 ml), dried over MgSO$_4$, and concentrated. The residue was purified by silica gel chromatography (AcOEt:hexane=1:4 to 1:1) to give 5.30 g (56% yield) of compound H8-C as a colorless solid.

mp 81°-83° C.;
$^1$HNMR (90 MHz, CDCl$_3$) δ 7.77 (s,1), 7.25-7.05 (m,15), 5.16 (m,2) 4.84 (m,1), 1.56 (s,3), 0.75 (s,9), -0.07 (s,3), -0.17 (s,3).

c) Preparation of compound H8-D:

(H8-D)

[Structure of H8-D]

To a solution of compound H8-C (1.0 g, 2.0 mmol) in methanol (10 ml) was passed ozonized oxygen (ca. 5 mmol) at −78° C. After the reaction mixture was flushed with nitrogen and dimethyl sulfide (1.48 ml, 20.2 mmol) was added at −78° C., the mixture was allowed to warm to room temperature, and stirred for 5 h. Concentration and purification by silica gel chromatography gave 780 mg (78% yield) of compound H8-D.

mp 80°-83° C.;
$^1$HNMR (90 MHz, CDCl$_3$) δ 7.81 (s,1), 7.25-6.99 (m,15), 5.11 (s,1) 2.19 (s,3), 0.76 (s,9), −0.04 (s,3).

d) Preparation of compound H8-E:

(H8-E)

[Structure of H8-E]

To a suspension of NaH (60% dispersion in mineral oil, 118 mg, 2,96 mmol) in 10 ml of toluene was added a solution of tetraethyl methylendiphosphonate (854 mg, 2.96 mmol) in 8 ml of toluene under nitrogen at room temperature. When a clear solution was formed, compound H8-D (1.34 g, 2.69 mmol) in 10 ml of toluene was added and stirred for 1 h at room temperature. A mixture of 45 ml of water and 90 ml of CHCl$_3$ was added and the aqueous layer was extracted with CHCl$_3$. The combined organic layers were dried over MgSO$_4$, concentrated, and purified by silica gel chromatography (AcOEt:hexane=1:1 to 10:1) to give 950 mg (56% yield) of the title compound as an oil.

$^1$HNMR (90 MHz, CDCl$_3$) δ 7.91 (s,1), 7.41-7.06 (m,15), 6.10 (broad d,1,J=18.0), 5.27 (m,1) 4.20-3.84 (m,4), 1.95 (d,3,J=3.3), 1.28 (t,3,J=7.0), 1.26 (t,3,J=7.0), 0.87 (s,9), 0.07 (s,3), −0.05 (s,3).

e) Preparation of compound H8-F:

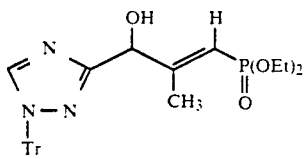
(H8-F)

To a solution of compound H8-E (840 mg) in 20 ml of THF was added n-Bu₄NF (0.42 mmol, 1.0 m in THF) under nitrogen at room temperature. After 30 min, the reaction mixture was diluted with 200 ml of water and extracted with CH₂Cl₂ (4×50 ml). The combined organic layers were dried over MgSO₄, concentrated, and purified by silica gel chromatography (AcOEt only) to give 510 mg (74% yield) of compound H8-F as a white solid.

mp 150°-152° C.;

¹HNMR (90 MHz, CDCl₃) δ 7.93 (s,1), 7.42-7.04 (m,15), 5.99 (broad d,1, J=17.4), 5.27 (m,1) 4.24-3.86 (m,4), 2.00 (dd,3, J=0.7,3.3), 1.26 (t,3, J=7.0), 1.24 (t,3, J=7.0).

f) Preparation of compound 1.056:

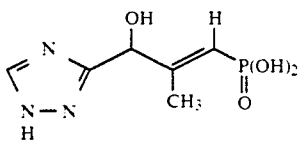

To a solution of compound H8-F (318 mg, 0.61 mmol) in 12 ml of CH₂Cl₂ was added trimethylsilyl bromide (0.41 ml, 3.07 mmol) under nitrogen at room temperature. After stirring for 16 h, methanol (6 ml) was added to the mixture and stirred for 2 h, and then propylene oxide (1.2 ml) was added. Ether was added slowly unitl precipitation was completed. Precipitates were collected and further purified with medium pressure liquid chromatography using a reverse phase column to afford 10 mg (7.4% yield) of the title compound.

mp 92°-105° C.;

¹HNMR (90 MHz, D₂O) δ 8.27 (broad s,1), 6.10 broad d,1, J=16.7), 5.50 (broad s,1), 1.92 (d,3, J=2.9).

EXAMPLE H9: PREPARATION OF COMPOUND 1.032

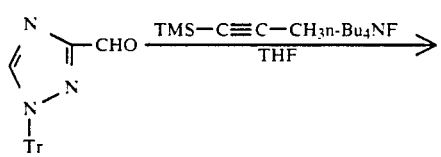

H-9A

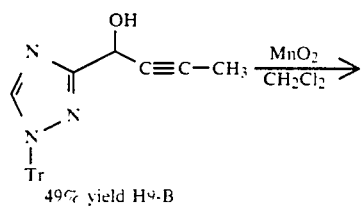

49% yield H9-B

-continued

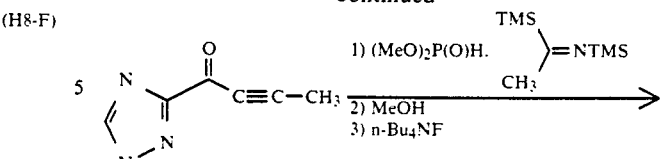

88% yield H9-C

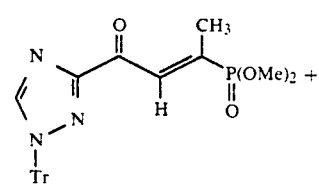

15% yield H9-D

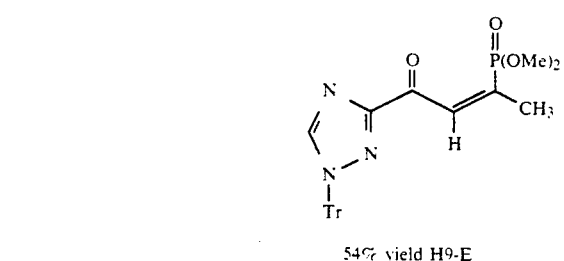

54% yield H9-E

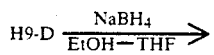

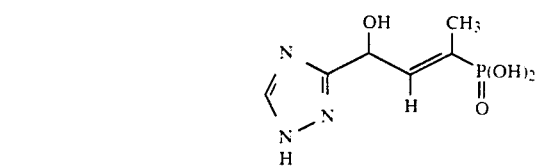

80% yield H9-F

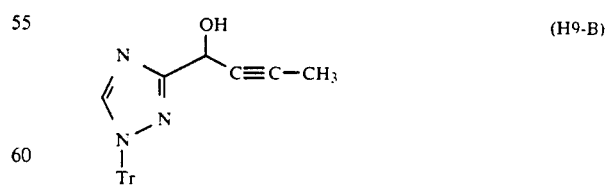

96% yield Compound 1.032 a) Preparation of compound H9-B:

(H9-B)

To a solution of aldehyde H9-A (10.0 g, 29.5 mmol) in 200 ml of THF were added 1-(trimethylsilyl)-1-propyne (5.01 ml, 33.9 mmol) and tetrabutylammonium fluoride (0.5 mmol, 1.0 m in THF) under nitrogen at 0° C. After stirring for 1.5 h at 0° C. and for 21 h at room temperature, the mixture was cooled to 0° C. and an additional tetrabutylammonium fluoride (8.5 mmol, 1.0 m in THF) was added. After 2 h, an additional 1-(trimethylsilyl)-1-propyne (2.18 ml, 14.7 mmol) was added to the mixture at 0° C. and the mixture was allowed to warm to room temperature and stirred for 30 min. The reaction mixture was diluted with 200 ml of water and extracted with AcOEt (3×100 ml). The combined organic layers were dried over MgSO4, concentrated, and purified by silica gel chromatography (AcOEt:hexane:CH2Cl2=2:2:1) to give 5.47 g (49% yield) of compound H9-B as a colorless solid.

mp 190°-194° C.;

¹HNMR (90 MHz, CDCl3) δ 7.93 (s,1), 7.42-7.06 (m,15), 5.48-5.65 (m,1), 3.25 (broad d, 1, J=7.7), 1.87 (d,3,J=2.4).

b) Preparation of compound H9-C:

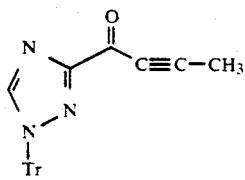

(H9-C)

To a suspension of compound H9-B (3.50 g, 9.22 mmol) in 140 ml of CH2Cl2 was added MnO2 (4.0 g, 46.1 mmol) in portions, and stirred for 70 min. After addition of Celite (8.0 g), the mixture was directly subjected to a silica gel column. Elution with a solvent mixture (AcOEt:hexane:CH2Cl2=2:2:1) afforded 3.06 g (88% yield) of compound H9-C as a colorless solid.

mp 151°-154° C.

¹HNMR (90 MHz, CDCl3) δ 8.02 (s,1), 7.40-7.10 (m,15), 2.12 (2,3).

c) Preparation of compound H9-D:

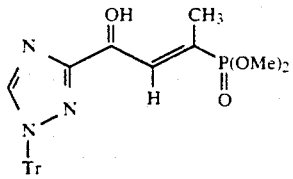

(H9-D)

To a solution of compound H9-C (3.0 g, 7.95 mmol) in 45 ml of CH2Cl2 were added dimethyl phosphite (0.87 ml, 9.54 mmol) and N,O-bis(trimethylsilyl)acetamide (2.14 ml, 8.74 mmol) under nitrogen at room temperature. After stirring for 4 h at room temperature, and for 21 h under reflux, methanol (20 ml) and n-Bu4NF (1.43 mmol, 1.0 m in THF) were added to the mixture at room temperature. After 1 h, the reaction was quenched by addition of water (100 ml) and extracted with CH2Cl2 (3×500 ml) and then with AcOEt (2×50 ml). The combined organic layers were dried over MgSO4, concentrated, and purified by silica gel chromatography (AcOEt:hexane:CH2Cl2=2:1:1) to afford 580 mg (15% yield) of the desired product as an oil, along with its stereo isomer H9-E (2.1 g, 54% yield).

H9-D ¹HNMR (90 MHz, CDCl3) δ 8.06 (s,1), 7.80 (broad d, 1, J=26.2), 7.40-7.01 (m,15), 3.74 (d,6, J=11.0), 2.32 (dd, 3, J=16.9, 1.6).

H9-E mp 140°-144° C.; ¹HNMR (90 MHz, CDCl3) δ 8.0 (s,1), 7.21 (broad d, 1, J=45.3.), 7.50-7.05 (m,15), 3.70 (d,6, J=11.0), 2.11 (dd, 3, J=13.4, 1.8).

d) Preparation of compound H9-F:

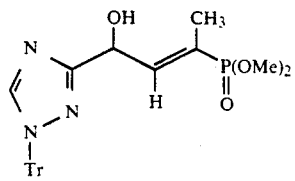

(H9-F)

To a solution of compound H9-D (400 mg, 0.821 mmol) in 10 ml of a solvent mixture (ethanol:THF=1:1) was added NaBH4 (15.5 mg, 0.41 mmol) under nitrogen at room temperature. After 15 min, water (50 ml) and sat. aq NH4Cl (1 ml) were added and the mixture was extracted with CH2Cl2 (2×30 ml) and with AcOEt (3×40 ml). The combined organic layers were dried over MgSO4, concentrated, and purified by silica gel chromatography (AcOEt only) to give 321 mg (80% yield) of compound H9-F as a colorless solid.

mp 158°-162° C.;

¹HNMR (90 MHz, CDCl3) δ 7.95 (s,1), 7.51-6.94 (m,15), 6.75 (ddd.1, J=23.3, 7.6, 1.4), 5.73-5.59 (m,1), 3.80 (dd,6, J=11.0, 5.5), 1.85 (dd,3, J=15.0, 1.5).

e) Preparation of compound 1.032:

$$\text{(1.032)}$$

To a solution of compound H9-F (280 mg, 0.57 mmol) in 8 ml of CH2Cl2 was added trimethylsilyl bromide (0.38 ml, 2.86 mmol) under nitrogen at room temperature. After 15 h, methanol (4 ml) was added and stirred for 2 h. After addition of propylene oxide (0.8 ml), ether was added slowly at 0° C. Resulting precipitates were collected, washed with ether, and dried to give 120 mg (96% yield) of the title compound as a white powder.

mp 97°-99° C. decomp.;

¹HNMR (90 MHz, D2O) δ 8.90 (s,1), 6.56-6.21 (m,1), 5.90 (dd,1, J=8.5, 2.5), 1.95 (dd,3, J=14.3, 1.1).

Compounds of the formulae Ia, Ib, Ic, Id, Ii, Ij and Ik which are listed in the Tables 1 to 7 are prepared analogously to Examples H1 to H9.

TABLE 1

Compounds of the formula Ia:

(Ia)

| Comp. No. | $R_1$ | $R_2$ | X | Y | $R_3$ | $R_4$ | Z | $R_5$ | $R_6$ |
|---|---|---|---|---|---|---|---|---|---|
| 1.001 | H | H | $C_2H_5$ | H | H | H | $C_2H_5$ | H | H |

TABLE 1-continued

Compounds of the formula Ia:

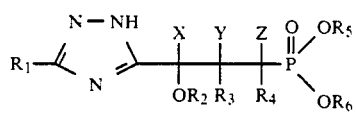

| Comp. No. | R₁ | R₂ | X | Y | R₃ | R₄ | Z | R₅ | R₆ |
|---|---|---|---|---|---|---|---|---|---|
| 1.002 | H | H | CH₃ | H | H | CH₃ | CH₃ | H | H |
| 1.003 | H | H | CH₃ | CH₃ | CH₃ | H | H | H | H |
| 1.004 | H | H | CH(CH₃)₂ | H | H | H | H | H | H |
| 1.005 | CH₃ | H | C₂H₅ | H | H | H | C₂H₅ | H | H |
| 1.006 | H | CCH₃‖O | C₂H₅ | H | H | H | H | H | C₂H₅ |
| 1.007 | H | H | C₂H₅ | H | H | H | C₂H₅ | C₂H₅ | C₂H₅ |
| 1.008 | H | H | CH₃ | H | H | H | H | H | H |
| 1.009 | H | H | C₂H₅ | H | H | H | H | H | H |
| 1.010 | H | H | (CH₂)₂CH₃ | H | H | H | H | H | H |
| 1.011 | H | H | (CH₂)₃CH₃ | H | H | H | H | H | H |
| 1.012 | H | H | H | H | bond | | H | H | H |
| 1.013 | H | H | CH₃ | H | CH₃ | H | H | H | H |
| 1.014 | H | CC₂H₅‖O | H | H | H | H | H | H | H |
| 1.015 | H | CC₃H₇-i‖O | H | H | H | H | H | H | H |
| 1.016 | H | 2,6-dichlorobenzoyl | H | H | H | H | H | H | H |
| 1.017 | H | 2,4-dichlorobenzoyl | H | H | H | H | H | H | H |
| 1.018 | H | 2,6-dichloro-3-methoxybenzoyl | H | H | H | H | H | H | H |
| 1.019 | H | 2,4-dichlorophenylacetyl | H | H | H | H | H | H | H |
| 1.020 | H | CCH₃‖O | CH₃ | H | H | H | H | H | H |
| 1.021 | H | 2,4-dichlorobenzoyl | CH₃ | H | H | H | H | H | H |
| 1.022 | H | CNHCH₃‖O | H | H | H | H | H | H | H |

TABLE 1-continued

Compounds of the formula Ia:

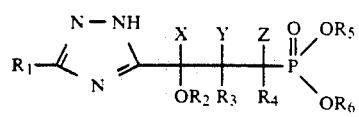

(Ia)

| Comp. No. | $R_1$ | $R_2$ | X | Y | $R_3$ | $R_4$ | Z | $R_5$ | $R_6$ |
|---|---|---|---|---|---|---|---|---|---|
| 1.023 | H | CNHC$_3$H$_7$-i ‖ O | H | H | H | H | H | H | H |
| 1.024 | H | CNH-Phenyl ‖ O | H | H | H | H | H | H | H |
| 1.025 | H | COCH$_3$ ‖ O | H | H | H | H | H | H | H |
| 1.026 | H | CN—(CH$_3$)OCH$_3$ ‖ O | H | H | H | H | H | H | H |
| 1.027 | H | COC$_3$H$_7$-i ‖ O | CH$_3$ | H | H | H | H | H | H |
| 1.028 | H | CN(C$_2$H$_5$)$_2$ ‖ O | H | H | H | H | H | H | H |
| 1.029 | H | H | CH$_3$ | H | bond | | H | H | H |
| 1.030 | H | H | CH$_3$ | H | H | H | CH$_3$ | H | H |
| 1.031 | H | H | CH$_3$ | H | H | CH$_3$ | H | H | H |
| 1.032 | H | H | H | H | bond | | CH$_3$ | H | H |
| 1.033 | H | CCH$_3$ ‖ O | H | H | bond | | CH$_3$ | H | H |
| 1.034 | H | H | CH$_3$ | H | bond | | CH$_3$ | H | H |
| 1.035 | H | CCH$_3$ ‖ O | CH$_3$ | H | bond | | CH$_3$ | H | H |
| 1.036 | H | H | H | H | bond | | H | H | CH$_3$ |
| 1.037 | H | CCH$_3$ ‖ O | H | H | bond | | H | H | H |
| 1.038 | H | H | CH$_3$ | CH$_3$ | bond | | H | H | H |
| 1.039 | H | CCH$_3$ ‖ O | CH$_3$ | CH$_3$ | bond | | H | H | H |
| 1.040 | H | H | H | H | bond | | CH$_3$ | H | H |
| 1.041 | H | CCH$_3$ ‖ O | H | H | bond | | CH$_3$ | H | H |
| 1.042 | H | H | CH$_3$ | CH$_3$ | bond | | CH$_3$ | H | H |
| 1.043 | H | CCH$_3$ ‖ O | CH$_3$ | CH$_3$ | bond | | CH$_3$ | H | H |
| 1.044 | H | H | CF$_3$ | H | H | H | H | H | H |
| 1.045 | H | H | ◁ | H | H | H | H | H | H |
| 1.046 | H | CCH$_2$OOCCH$_3$ ‖ O | H | H | H | H | H | H | H |

TABLE 1-continued

Compounds of the formula Ia:

$$R_1 \stackrel{N-NH}{\underset{N}{\diagdown}} \stackrel{X\ Y\ Z}{\underset{OR_2\ R_3\ R_4}{-C-C-C-}} \stackrel{O}{\underset{OR_6}{\overset{\parallel}{P}}} OR_5 \qquad (Ia)$$

| Comp. No. | R₁ | R₂ | X | Y | R₃ | R₄ | Z | R₅ | R₆ |
|---|---|---|---|---|---|---|---|---|---|
| 1.047 | H | COCH₂COOC₂H₅ (C=O) | H | H | H | H | H | H | H |
| 1.048 | H | H | CH₂OH | H | H | H | H | H | H |
| 1.049 | H | C(=O)(CH₂)₅CH₃ | H | H | H | H | H | H | H |
| 1.050 | H | COCH₂CH₃ (C=O) | H | H | H | H | H | H | H |
| 1.051 | CH₃ | H | H | H | H | H | H | H | H |
| 1.052 | H | CCH₃ (C=O) | CH₃ | H | H | H | H | H | H |
| 1.053 | H | C(=O)-cyclopropyl | H | H | H | H | H | H | H |
| 1.054 | H | C(=O)t-Butyl | H | H | H | H | H | H | H |
| 1.055 | H | CSCH₂CH₃ (C=O) | H | H | H | H | H | H | H |
| 1.056 | H | H | H | CH₃ | bond | | H | H | H |
| 1.057 | CH₃ | H | H | H | H | H | H | H | H |

TABLE 2

Compounds of the formula Ib:

$$R_1 \stackrel{N-NH}{\underset{N}{\diagdown}} \stackrel{R_7\ R_8}{\underset{OR_2\ R_4}{-C-}} \stackrel{(CH_2)_n}{\underset{}{\diagdown}} \stackrel{OR_5}{\underset{O\ OR_6}{\overset{\parallel}{P}}} \qquad (Ib)$$

| Comp. No. | Isom. | R₁ | R₂ | n | R₄ | R₇ | R₈ | R₅ | R₆ |
|---|---|---|---|---|---|---|---|---|---|
| 2.001 | | H | H | 1 | H | H | H | C₂H₅ | C₂H₅ |
| 2.002 | trans | H | H | 1 | H | H | H | H | H |
| 2.003 | | H | H | 0 | CH₃ | H | H | H | H |
| 2.004 | | H | H | 1 | CH₃ | CH₃ | CH₃ | H | H |
| 2.005 | | H | H | 1 | CH₃ | H | H | CH₂-C₆H₅ | CH₂-C₆H₅ |
| 2.006 | | CH₃ | H | 1 | CH₃ | H | H | H | H |
| 2.007 | | H | CCH₃ (C=O) | 1 | H | H | H | H | H |
| 2.008 | | H | C(=O)NH-C₆H₅ | 1 | H | H | H | H | H |

TABLE 2-continued

Compounds of the formula Ib:

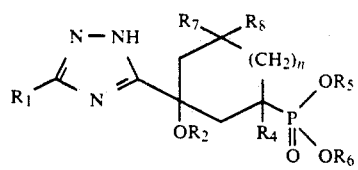

| Comp. No. | Isom. | $R_1$ | $R_2$ | n | $R_4$ | $R_7$ | $R_8$ | $R_5$ | $R_6$ |
|---|---|---|---|---|---|---|---|---|---|
| 2.009 | trans | H | H | 1 | $CH_3$ | H | H | H | H |
| 2.010 | cis | H | H | 2 | H | H | H | H | H |

TABLE 3

Compounds of the formula Ic:

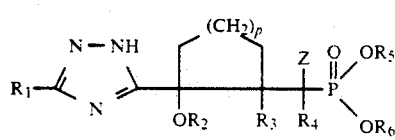

| Compound No. | $R_1$ | $R_2$ | p | $R_3$ | Z | $R_4$ | $R_5$ | $R_6$ |
|---|---|---|---|---|---|---|---|---|
| 3.001 | H | H | 1 | H | H | H | H | H |
| 3.002 | H | H | 2 | H | H | H | H | H |

TABLE 4

Compounds of the formula Id:

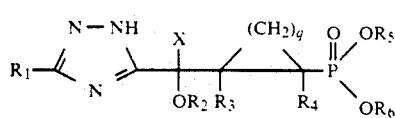

| Compound No. | $R_1$ | $R_2$ | X | q | $R_3$ | $R_4$ | $R_5$ | $R_6$ |
|---|---|---|---|---|---|---|---|---|
| 4.001 | H | H | H | 1 | H | H | H | H |
| 4.002 | H | H | $CH_3$ | 2 | H | H | H | H |
| 4.003 | H | H | $CH_3$ | 3 | H | H | H | H |
| 4.004 | H | H | H | 4 | H | H | H | H |
| 4.005 | H | H | $CH_3$ | 4 | H | H | H | H |

TABLE 5

Compounds of the formula Ii:

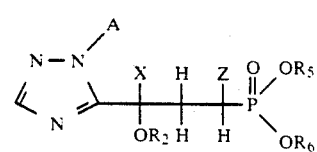

| Comp. No. | Isomer | A | X | Z | $R_2$ | $R_5$ | $R_6$ |
|---|---|---|---|---|---|---|---|
| 5.001 | | $CH_3$ | $CH_3$ | H | H | H | H |
| 5.002 | cis | $CH_3$ | $-(CH_2)_3-$ | — | H | H | H |
| 5.003 | trans | $CH_3$ | $-(CH_2)_3-$ | — | H | H | H |
| 5.004 | | $CH_2CH_2CH_3$ | $CH_3$ | H | H | H | H |
| 5.005 | cis | $CH_2CH_3$ | $-(CH_2)_3-$ | — | H | H | H |
| 5.006 | trans | $CH_2CH_3$ | $-(CH_2)_3-$ | — | H | H | H |
| 5.007 | | $CH_2CH_3$ | $CH_3$ | H | H | H | H |
| 5.008 | cis | $CH_3$ | $-(CH_2)_2-$ | — | H | H | H |
| 5.009 | trans | $CH_3$ | $-(CH_2)_2-$ | — | H | H | H |
| 5.010 | | $CH_3$ | $CH_3$ | H | $\underset{O}{\overset{\parallel}{C}CH_3}$ | H | H |
| 5.011 | | allyl | $CH_3$ | H | H | H | H |
| 5.012 | | $CH_2CH_2OH$ | $CH_3$ | H | H | H | H |

TABLE 6

Compounds of the formula Ij:

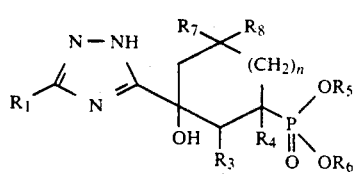

| Comp. No. | Isomer | $R_1$ | $R_3$ | n | $R_4$ | $R_7$ | $R_8$ | $R_5$ | $R_6$ |
|---|---|---|---|---|---|---|---|---|---|
| 6.001 | trans | H | $CH_3$ | 1 | H | H | H | H | H |
| 6.002 | | H | H | 1 | $CH_3$ | H | H | H | H |
| 6.003 | | H | H | 0 | $CH_3$ | H | H | H | H |
| 6.004 | | H | H | 1 | $CH_3$ | $CH_3$ | $CH_3$ | H | H |
| 6.005 | | H | H | 1 | $CH_3$ | H | H | 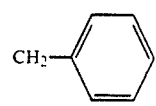 | 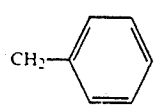 |
| 6.006 | | $CH_3$ | H | 1 | $CH_3$ | H | H | H | H |

TABLE 6-continued

Compounds of the formula Ij:

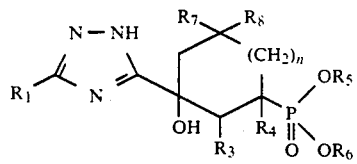

| Comp. No. | Isomer | $R_1$ | $R_3$ | n | $R_4$ | $R_7$ | $R_8$ | $R_5$ | $R_6$ |
|---|---|---|---|---|---|---|---|---|---|
| 6.007 | | H | $C_2H_5$ | 1 | H | H | H | H | H |
| 6.008 | | H | $n\text{-}C_3H_7$ | 1 | H | H | H | H | H |

TABLE 7

Compounds of the formula Ik:

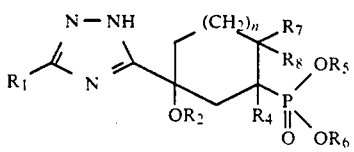

| Comp. No. | Isom. | $R_1$ | $R_2$ | n | $R_4$ | $R_7$ | $R_8$ | $R_5$ | $R_6$ |
|---|---|---|---|---|---|---|---|---|---|
| 7.001 | cis | H | H | 1 | H | $CH_3$ | $CH_3$ | H | H |
| 7.002 | trans | H | H | 1 | H | $CH_3$ | $CH_3$ | H | H |

TABLE 8

Physical data of the compounds of the formula I:

| | |
|---|---|
| 1.002 | m.p. 175–176° C. (decomp.) |
| 1.009 | m.p. 155–158° C. |
| 1.010 | m.p. 87° C. (decomp.) |
| 1.013 | m.p. 80° C. (decomp.) |
| 1.014 | m.p. 80–80° C. (decomp.) |
| 1.015 | m.p. 98° C. (decomp.) |
| 1.017 | m.p. 127° C. (decomp.) |
| 1.019 | m.p. 78° C. (decomp.) |
| 1.022 | m.p. 96° C. (decomp.) |
| 1.023 | m.p. 103° C. (decomp.) |
| 1.024 | m.p. 151° C. (decomp.) |
| 1.025 | m.p. 96° C. (decomp.) |
| 1.028 | m.p. 85° C. (decomp.) |
| 1.030 | m.p. 80° C. 3(S),2(R)-configuration |
| 1.031 | m.p. 80° C. 3(S),2(S)-configuration |
| 1.032 | m.p. 97–99° C. (decomp.) |
| 1.045 | m.p. 112° C. (decomp.) |
| 1.046 | m.p. 99° C. (decomp.) |
| 1.047 | m.p. 90° C. (decomp.) |
| 1.049 | m.p. 78° C. |
| 1.050 | m.p. 88° C. (decomp.) |
| 1.051 | solid |
| 1.052 | m.p. 135–140° C. |
| 1.053 | m.p. 85° C. (decomp.) |
| 1.054 | m.p. 193–195° C. |
| 1.055 | m.p. 98° C. (decomp.) |
| 1.056 | m.p. 92–105° C. (decomp.) |
| 2.002 | m.p. 166° C. (decomp.) |
| 2.004 | m.p. 195–198° C. |
| 2.007 | m.p. 184–186° C. |
| 2.009 | m.p. 210–212° C. |
| 2.012 | m.p. 197–198° C. (decomp.) |
| 5.001 | m.p. 188–191° C. |
| 5.002 | m.p. 120–125° C. |
| 5.003 | m.p. 226–229° C. |
| 5.004 | m.p. 146–148° C. |
| 5.006 | m.p. 213–218° C. |
| 5.007 | m.p. 152–155° C. |
| 5.008 | m.p. 170–174° C. |
| 5.009 | m.p. 230–235° C. |
| 5.011 | m.p. 126–127.5° C. |
| 6.001 | m.p. 201–203° C. (decomp.) |
| 7.001 | m.p. 125° C. (decomp.) |

TABLE 8-continued

Physical data of the compounds of the formula I:

| | |
|---|---|
| 7.002 | m.p. 168° C. (decomp.) |

Formulation examples of active substances of the formula I (% = percent by weight)

| 1. Emulsion concentrates | a) | b) |
|---|---|---|
| Active substance from Table 1-7 | 10% | 1% |
| Ca dodecylbenzenesulfonate | 3% | 3% |
| Octylphenol polyethylene glycol ether (4–5 mol of EO) | 3% | 3% |
| Castor oil polyethylene glycol ether (36 mol of EO) | 4% | 4% |
| Cyclohexanone | 30% | 10% |
| Xylene mixture | 50% | 79% |

Emulsions of any desired concentration can be prepared from such concentrates by diluting them with water.

| 2. Suspension concentrate | a) | b) |
|---|---|---|
| Active substance from Table 1-7 | 5% | 40% |
| Ethylene glycol | 10% | 10% |
| Nonylphenol polyethylene glycol ether (15 mol of EO) | 1% | 6% |
| Na ligninsulfonate | 5% | 10% |
| Carboxymethylcellulose | 1% | 1% |
| 37% aqueous formaldehyde solution | 0.2% | 0.2% |
| Silicone oil in the form of a 75% aqueous emulsion | 0.8% | 0.8% |
| Water | 77% | 32% |

The finely-ground active substance is mixed intimately with the additives. This gives a suspension concentrate, from which suspensions of any desired concentration can be prepared by diluting it with water.

| 3. Salt solution | |
|---|---|
| Active substance from Table 1-7 | 5% |
| Isopropylamine | 1% |
| Octylphenol polyethylene glycol ether (78 mol of EO) | 3% |
| Water | 91% |

The compounds of the formula I are employed as such or preferably as compositions together with the auxiliaries customary in formulation technology, and they are therefore processed in a known manner to give, for example, emulsion concentrates, directly sprayable or dilutable solutions, dilute emulsions, sprayable powders, soluble powders, dusts, granules, and also encapsulations, for example in polymeric substances. The application methods, such as spraying, atomising, dusting, scattering or pouring, as well as the type of compositions are selected to suit the intended aims and the prevailing circumstances.

BIOLOGICAL EXAMPLES

EXAMPLE B1: HERBICIDAL ACTION BEFORE EMERGENCE OF THE PLANTS

The test plants are seeded out in plastic pots containing standard soil. Immediately after seeding, the pots are beeing sprayed with an aqueous suspension of the compound No. 2.002. The rate corresponds to 4000 g a.i./ha. The treated pots are then placed in the greenhouse at temperatures of 18° C. (night) and 24° C. (day). Appr. 3 weeks after treatment, the emerged plants are evaluated in terms of herbicidal symptoms:
1: plants have not emerged or are totally withered
2-3: very pronounced action
4-6: medium action
7-8: weak action
9: no action (as untreated controls).

In this test, the compound 2.002 given in Table 2 shows very pronounced herbicidal action (rating "3") against the weed "Setaria".

EXAMPLE B2: POST-EMERGENCE HERBICIDAL ACTION (CONTACT HERBICIDE)

The test plants are seeded out in plastic pots containing standard soil and raised in the greenhouse at 18° C. (night) and 24° C. (day). Appr. 10 to 20 days after seeding (depending of individual growth-rate), foliar treatment takes place with an aqueous suspension of compound No. 2.002. The rate corresponds to 4000 g a.i./ha. Appr. 2 weeks after treatment, the emerged plants are evaluated in terms of herbicidal symptoms:
1: plants have not emerged or are totally withered
2-3: very pronounced action
4-6: medium action
7-8: weak action
9: no action (as untreated controls).

In this test, the compound 2.002 given in Table 2 shows very pronounced herbicidal action (rating "3") against the weed "Stellaria" and medium action (rating "4" against the weed "Sinapis".

EXAMPLE B3: POST-EMERGENCE HERBICIDAL ACTION (CONTACT HERBICIDE)

The test plants are seeded out in plastic pots containing standard soil and raised in the greenhouse at 18° C. (night) and 24° C. (day). Appr. 10 to 20 days after seeding (depending of individual growth-rate), foliar treatment takes place with an aqueous suspension of compound No. 5.001. The rate corresponds to 2000 g a.i./ha. Appr. 2 weeks after treatment, the emerged plants are evaluated in terms of herbicidal symtoms:
1: plants have not emerged or are totally withered
2-3: very pronounced action
4-6: medium action
7-8: weak action
9: no action (as untreated controls).

In this test, the compound 5.001 given in Table 5 shows very pronounced herbicidal action (rating "3") against the weeds "Stellaria" and "Setaria".

What is claimed is:
1. A triazole of the formula I

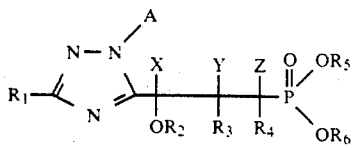

in which
A is hydrogen, $C_1-C_4$-alkyl, $C_1-C_4$-alkenyl, triphenylmethyl, benzyl, a group

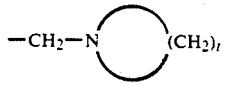

or $C_1-C_4$-alkyl substituted by hydroxy or $C_1-C_4$-alkoxy;
t is 4 or 5;
$R_1$ is hydrogen; fluorine or $C_1-C_4$-alkyl;
$R_2$ is hydrogen, a group

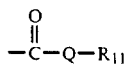

or a group

$R_3$ is hydrogen or $C_1-C_4$-alkyl;
$R_4$ is hydrogen or $C_1-C_4$-alkyl, or $R_3$ and $R_4$ together represent a chemical bond;
$R_5$ is hydrogen, $C_1-C_4$-alkyl, benzyl or an alkali metal alkaline earth metal ammonium organic ammonium, tri-$C_1-C_6$-alkyl-sulphoniam, tri-$C_1-C_6$-alkyl-sulfoxonium, phosphonium or amidinium cation;
$R_6$ is hydrogen, $C_1-C_4$-alkyl, benzyl or an alkali metal alkaline earth metal, ammonium, organic ammonium, tri-$C_1-C_6$-alkyl-sulphoniam, tri-$C_1-C_6$-alkyl-sulfoxonium, phosphonium or amidinium cation;
X is hydrogen, $C_1-C_4$-alkyl, $C_3-C_6$-cycloalkyl, $C_1-C_4$-haloalkyl, $C_1-C_4$-alkyl substituted by hydroxy or $C_1-C_4$-alkyl substituted by —$OR_{14}$;
Y is hydrogen or $C_1-C_4$-alkyl or together with X a —$CH_2$—($CH_2)_p$—$CH_2$— group or together with Z a $C_1-C_4$-alkylene bridge which is substituted by $R_7$ and $R_8$;
Z is hydrogen or $C_1-C_4$-alkyl or together with X a $C_2-C_4$-alkylene bridge which is substituted by $R_7$ and $R_8$;
Q is oxygen, sulfur or $NR_{10}$;
$R_7$ is hydrogen, $C_1-C_4$-alkoxy or $C_1-C_4$-alkyl;
$R_8$ is hydrogen, $C_1-C_4$-alkoxy or $C_1-C_4$-alkyl;
$R_9$ is $C_1-C_6$-alkyl, $C_2-C_6$-alkenyl, $C_2-C_6$-alkynyl; or $C_1-C_6$-alkyl, $C_2-C_6$-alkenyl, $C_2-C_6$-alkynyl substituted by halogen or $C_1-C_4$-alkoxy; or phenyl, benzyl; or phenyl, benzyl substituted by $C_1-C_4$-alkyl, halogen, $C_1-C_4$-haloalkyl, $C_1-C_4$-alkoxy, cyano, nitro, $C_1-C_4$-alkoxycarbonyl or $S(O)_m$—$C_1-C_4$-alkyl; or is $C_1-C_6$-alkoxyalkyl, $C_1-C_6$-alkylcarbonyloxyalkyl, $C_1-C_6$-alkoxycarbonylalkyl or $C_3-C_6$-cycloalkyl;
$R_{10}$ is hydrogen, $C_1-C_6$-alkyl, $C_1-C_6$-alkoxy, $C_2-C_6$-alkenyl, $C_3-C_6$-alkynyl; or $C_1-C_6$-alkyl, $C_2-C_6$- alkenyl, $C_3$-$C_6$-alkynyl substituted by halogen or $C_1$-$C_4$-alkoxy;

$R_{11}$ is $C_1$-$C_6$-alkyl, $C_3$-$C_6$-alkenyl, $C_3$-$C_6$-alkynyl; or $C_1$-$C_6$-alkyl, $C_3$-$C_6$-alkenyl, $C_3$-$C_6$-alkynyl substituted by halogen or $C_1$-$C_4$-alkoxy; or phenyl, benzyl; or phenyl, benzyl substituted by $C_1$-$C_4$-alkyl, halogen, halomethyl, $C_1$-$C_4$-alkoxy, cyano, nitro, $C_1$-$C_4$-alkoxycarbonyl or $S(O)_n$—$C_1$-$C_4$-alkyl;

$R_{14}$ is hydrgoen, a group

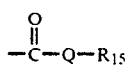

or a group

$R_{15}$ is $C_1$-$C_6$-alkyl, $C_3$-$C_6$-alkenyl, $C_3$-$C_6$-alkynyl; or $C_1$-$C_6$-alkyl, $C_3$-$C_6$-alkenyl, $C_3$-$C_6$-alkynyl substituted by halogen or $C_1$-$C_4$-alkoxy; or phenyl, benzyl; or phenyl, benzyl substituted by $C_1$-$C_4$-alkyl, halogen, halomethyl, $C_1$-$C_4$-alkoxy, cyano, nitro, $C_1$-$C_4$-alkoxycarbonyl or $S(O)_n$—$C_1$-$C_4$-alkyl;

$R_{16}$ is $C_1$-$C_6$-alkyl, $C_2$-$C_6$-alkenyl, $C_2$-$C_6$-alkynyl; or $C_1$-$C_6$-alkyl, $C_2$-$C_6$-alkenyl, $C_2$-$C_6$-alkynyl substituted by halogen or $C_1$-$C_4$-alkoxy; or phenyl, benzyl; or phenyl, benzyl substituted by $C_1$-$C_4$-alkyl, halogen, $C_1$-$C_4$-haloalkyl, $C_1$-$C_4$-alkoxy, cyano, nitro, $C_1$-$C_4$-alkoxycarbonyl or $S(O)_m$—$C_1$-$C_4$-alkyl; or is $C_1$-$C_6$-alkoxyalkyl, $C_1$-$C_6$-alkylcarbonyloxyalkyl, $C_1$-$C_6$-alkoxycarbonylalkyl or $C_3$-$C_6$-cycloalkyl;

m is 0, 1 or 2;
n is 0, 1 or 2;
p is 1 or 2;

with the proviso that $R_1$, $R_2$, $R_3$, $R_4$, X, Y and Z are not simultaneously hydrogen; and if $R_1$, $R_3$, $R_4$, X, Y and Z are simultaneously hydrogen, $R_9$ is not methyl.

2. A compound according to claim 1, in which
A is hydrogen, $C_1$-$C_4$-alkyl, triphenylmethyl, benzyl or a group

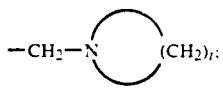

t is 4 or 5;
$R_1$ is hydrogen, fluorine or $C_1$-$C_4$-alkyl;
$R_2$ is hydrogen, a group

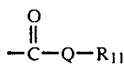

or a group

$R_3$ is hydrogen or $C_1$-$C_4$-alkyl;
$R_4$ is hydrogen or $C_1$-$C_4$-alkyl, or $R_3$ and $R_4$ together represent a chemical bond;

$R_5$ is hydrogen, $C_1$-$C_4$-alkyl, benzyl or an alkali metal, alkaline earth metal, ammonium, organic ammonium, tri-$C_1C_6$-alkyl-sulphonium, tri-$C_1C_6$-alkylsulfoxonium, phosphonium or amidinium cation;

$R_6$ is hydrogen, $C_1$-$C_4$-alkyl, benzyl or an alkali metal, alkaline earth metal, ammonium, organic ammonium, tri-$C_1C_6$-alkyl-sulphonium, tri-$C_1C_6$alkylsulfoxonium, phosphonium or amidinium cation;

X is hydrogen or $C_1$-$C_4$-alkyl;
Y is hydrogen or $C_1$-$C_4$-alkyl or together with X a —$CH_2$—$(CH_2)_p$—$CH_2$— group or together with Z a $C_1$-$C_4$-alkylene bridge which is substituted by $R_7$ and $R_8$;
Z is hydrogen or $C_1$-$C_4$-alkyl or together with X a $C_2$-$C_4$-alkylene bridge which is substituted by $R_7$ and $R_8$;
Q is oxygen, sulfur or $NR_{10}$;
$R_7$ is hydrogen, $C_1$-$C_4$-alkoxy or $C_1$-$C_4$-alkyl;
$R_8$ is hydrogen, $C_1$-$C_4$-alkoxy or $C_1$-$C_4$-alkyl;
$R_9$ is $C_1$-$C_6$-alkyl, $C_2$-$C_6$-alkenyl, $C_2$-$C_6$-alkynyl; or $C_1$-$C_6$-alkyl, $C_2$-$C_6$-alkenyl, $C_2$-$C_6$-alkynyl substituted by halogen or $C_1$-$C_4$-alkoxy; or phenyl, benzyl; or phenyl, benzyl substituted by $C_1$-$C_4$-alkyl, halogen, $C_1$-$C_4$-haloalkyl, $C_1$-$C_4$-alkoxy, cyano, nitro, $C_1$-$C_4$-alkoxycarbonyl or $S(O)_m$—$C_1$-$C_4$-alkyl;
$R_{10}$ is hydrogen, $C_1$-$C_6$-alkyl, $C_1$-$C_6$-alkoxy, $C_2$-$C_6$-alkenyl, $C_3$-$C_6$-alkynyl; or $C_1$-$C_6$-alkyl, $C_2$-$C_6$-alkenyl, $C_3$-$C_6$-alkynyl substituted by halogen or $C_1$-$C_4$-alkoxy;
$R_{11}$ is $C_1$-$C_6$-alkyl, $C_3$-$C_6$-alkenyl, $C_3$-$C_6$-alkynyl; or $C_1$-$C_6$-alkyl, $C_3$-$C_6$-alkenyl, $C_3$-$C_6$-alkynyl substituted by halogen or $C_1$-$C_4$-alkoxy; or phenyl, benzyl; or phenyl, benzyl substituted by $C_1$-$C_4$-alkyl, halogen, halomethyl, $C_1$-$C_4$-alkoxy, cyano, nitro, $C_1$-$C_4$-alkoxycarbonyl or $S(O)_n$—$C_1$-$C_4$-alkyl;

m is 0, 1 or 2;
n is 0, 1 or 2;
p is 1 or 2;

with the proviso that $R_1$, $R_2$, $R_3$, $R_4$, X, Y, and Z are not simultaneously hydrogen; and if $R_1$, $R_3$, $R_4$, X, Y and Z are simultaneously hydrogen, $R_9$ is not methyl.

3. A compound of the formula I according to claim 1, in which

A is hydrogen, triphenylmethyl, benzyl or a group

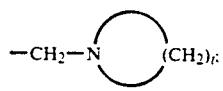

$R_2$ is hydrogen or a group

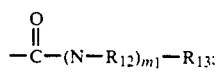

$R_{12}$ is hydrogen or $C_1$-$C_4$-alkyl;
$m_1$ is 0 or 1;
$R_{13}$ is $C_1$-$C_4$-alkyl, methoxy, trifluoromethyl, phenyl, benzyl, phenyl substituted by halogen or methoxy; or benzyl substituted by halogen, methoxy, methylthio, cyano or trifluoromethyl.

4. A compound of the formula I according to claim 1, in which

A is hydrogen;

$R_5$ is hydrogen or an alkali metal, alkaline earth metal, ammonium, organic ammonium, tri-$C_1C_6$-alkylsulphonium, tri-$C_1C_6$-alkylsufoxonium, phosphonium or amidinium cation; and $R_6$ is hydrogen or an alkali metal, alkaline earth metal, ammonium, organic ammonium, tri-$C_1C_6$-alkylsulphonium, tri-$C_1C_6$-alkylsulfoxonium, phosphonium or amidinium cation.

5. A compound of the formula I according to claim 1, in which $R_1$ and A are hydrogen.

6. A compound of the formula I according to claim 1, in which $R_2$ and A are hydrogen.

7. A compound according to claim 1 of the formula

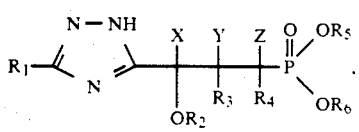

(Ia)

wherein $R_1$, $R_2$, $R_3$, $R_4$, $R_5$, $R_6$, X, Y and Z have the meaning given in claim 1.

8. A compound according to claim 6, in which $R_1$ is hydrogen or methyl; $R_2$ is hydrogen or acetyl; $R_3$ is hydrogen or methyl; $R_4$ is hydrogen or methyl; $R_5$ is hydrogen or ethyl; $R_6$ is hydrogen or ethyl; X is methyl, ethyl or isopropyl; Y is hydrogen or methyl; and Z is hydrogen, methyl or ethyl.

9. A compound according to claim 1 of the formula

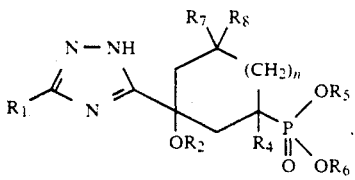

(Ib)

wherein $R_1$, $R_2$, $R_4$, $R_5$, $R_6$, $R_7$ and $R_8$ have the meaning given in claim 1 and n is 0, 1 or 2.

10. A compound according to claim 9 in which $R_1$ is hydrogen or methyl; $R_2$ is hydrogen, acetyl or N-phenyl carbamoyl; n is 0 or 1; $R_4$ is hydrogen or methyl; $R_5$ is hydrogen, ethyl or benzyl; $R_6$ is hydrogen, ethyl or benzyl; $R_7$ is hydrogen or methyl; and $R_8$ is hydrogen or methyl.

11. A compound according to claim 1 of the formula

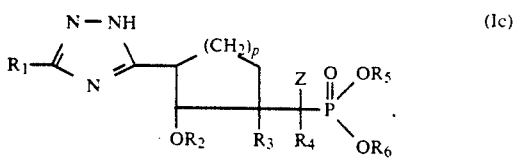

(Ic)

wherein $R_1$, $R_2$, $R_3$, $R_4$, $R_5$, $R_6$, Z and p have the meaning given in claim 1.

12. A compound according to claim 11 in which $R_1$, $R_2$, $R_3$, $R_4$, $R_5$, $R_6$ and Z each is hydrogen and p is 1 or 2.

13. A compound according to claim 1 of the formula

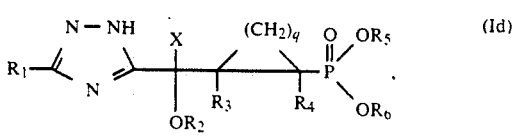

(Id)

wherein $R_1$, $R_2$, $R_3$, $R_4$, $R_5$, $R_6$ and X have the meaning given in claim 1 and q is 1, 2, 3 or 4.

14. A compound according to claim 13, wherein $R_1$, $R_2$, $R_3$, $R_4$, $R_5$ and $R_6$ each is hydrogen; X is hydrogen or methyl; and q is 1, 2, 3 or 4.

15. A compound according to claim 1, wherein A is hydrogen and $R_2$ is a group

16. trans-3-Hydroxy-3-(1,2,4-triazole-3-yl)-cyclohexyl-phosphonic acid according to claim 1.

17. A herbicidal and plant-growth-inhibiting composition, which comprises an effective amount of a triazole of the formula I according to claim 1 and an inert carrier.

18. A composition according to claim 17, which comprises between 0.1% and 95% of active substance of the formula I according to claim 1.

19. A method of controlling undesired plant growth, which comprises applying an effective amount of an active substance of the formula I according to claim 1, or a composition comprising this active substance according to claim 17, to the plants or their environment.

20. A method according to claim 19, in which an amount of active substance of between 0.005 and 2 kg is applied per hectare.

* * * * *

Adverse Decisions In Interference

Patent No. 5,248,655, Kenji Hayakawa, Ichiro Mori, Genji Jwasaki, Shin-Ichiro Matsunaga, 1,2,4-TRIAZOLE-3-YL-ALKANE-OR CYCLOALKANE-PHOSPHONIC ACIDS, AS ACTIVE SUBSTANCES IN WEED KILLERS, Interference No. 103,813, final judgment adverse to the patentees rendered February 9, 1998, as to claims 1-20.

*(Official Gazette June 2, 1998)*